(12) United States Patent
Barf et al.

(10) Patent No.: US 7,094,792 B2
(45) Date of Patent: Aug. 22, 2006

(54) INHIBITORS OF 11-BETA-HYDROXY STEROID DEHYDROGENASE TYPE 1

(75) Inventors: Tjeerd Barf, Uppsala (SE); Rikard Emond, Saltsjöbaden (SE); Guido Kurz, Stockholm (SE); Marianne Nilsson, Rimbo (SE); Jerk Vallgårda, Uppsala (SE); Lian Zhang, Södertälje (SE)

(73) Assignee: Biovitrum AB, Stockholm (SE)

( * ) Notice: Subject to any disclaimer, the term of this patent is extended or adjusted under 35 U.S.C. 154(b) by 221 days.

(21) Appl. No.: 10/302,036

(22) Filed: Nov. 22, 2002

(65) Prior Publication Data

US 2003/0130318 A1    Jul. 10, 2003

Related U.S. Application Data

(60) Provisional application No. 60/348,617, filed on Jan. 14, 2002.

(30) Foreign Application Priority Data

Nov. 22, 2001   (SE) .................................... 0103911

(51) Int. Cl.
A61K 31/426    (2006.01)
C07D 277/52    (2006.01)

(52) U.S. Cl. ...................................... 514/365; 548/204

(58) Field of Classification Search ................ 548/198, 548/204; 514/370, 365
See application file for complete search history.

(56) References Cited

U.S. PATENT DOCUMENTS

| | | |
|---|---|---|
| 2,362,087 A | 11/1944 | Newbery |
| 4,254,260 A | 3/1981 | Takaya et al. |
| 5,403,857 A | 4/1995 | Edwards et al. |
| 5,594,021 A | 1/1997 | Chan et al. |
| 5,783,597 A | 7/1998 | Beers et al. |
| 5,856,347 A | 1/1999 | Hashiguchi et al. |
| 5,962,490 A | 10/1999 | Chan et al. |
| 6,030,991 A | 2/2000 | Chan et al. |
| 2003/0130258 A1 | 7/2003 | Kurz et al. |
| 2003/0130279 A1 | 7/2003 | Kurz et al. |
| 2003/0166689 A1 | 9/2003 | Kurz et al. |
| 2003/0176476 A1 | 9/2003 | Barf et al. |
| 2003/0199501 A1 | 10/2003 | Nilsson et al. |

FOREIGN PATENT DOCUMENTS

| | | |
|---|---|---|
| EP | 749 964 A1 | 12/1996 |
| EP | 0 790 057 A1 | 8/1997 |
| EP | 819 681 A2 | 1/1998 |
| EP | 1 069 114 A2 | 1/2001 |
| FR | 94.123 | 1/1968 |
| FR | 2 384 498 | 10/1978 |
| GB | 620 654 | 3/1949 |
| GB | 822 947 | 11/1959 |
| JP | 2001483 A | 1/1990 |
| JP | 03173876 A | 7/1991 |
| JP | 687841 A | 3/1994 |
| NL | 6610324 | 1/1967 |
| WO | WO 96/04912 A1 | 2/1996 |
| WO | WO 97/07789 A1 | 3/1997 |
| WO | WO 98/16520 A1 | 4/1998 |
| WO | WO 98/27081 A1 | 6/1998 |
| WO | WO 98/36770 A1 | 8/1998 |
| WO | WO 99/02502 | 1/1999 |
| WO | WO 99/65884 A1 | 12/1999 |
| WO | WO 00/02851 A1 | 1/2000 |
| WO | WO 01/01971 A1 | 1/2001 |
| WO | WO 01/52833 A1 | 7/2001 |
| WO | WO 01/54691 A | 8/2001 |
| WO | WO 01/90090 A1 | 11/2001 |
| WO | WO 01/90091 A1 | 11/2001 |
| WO | WO 02/28353 A2 | 4/2002 |
| WO | WO 03/011258 A1 | 2/2003 |

OTHER PUBLICATIONS

Chemcats, "5-Thiazolecarboxylic acid, 4-methyl-2-(((4-methylphenyl)sulfonyl)amino)-, ethyl ester," Pharma Library Collection, (May 14, 2001). Chemcats Accession No. 2001:20962, Order No. NS46076, CAS Registry No. 313230-18-1.

Chemcats, "5-Thiazolecarboxylic acid, 2-(((4-chlorophenyl)sulfonyl)amino)-4-methyl-, ethyl ester," Pharma Library Collection, (May 14, 2001). Chemcats Acccession No. 2001:19109, Order No. NS41693, CAS Registry No. 312915-26-7.

Chemcats, "5-Thiazolecarboxylic acid, 4-methyl-2-(((3-nitrophenyl)sulfonyl)amino)-, ethyl ester," ChemDiv, Inc. Product Library, (Apr. 26, 2001). Chemcats Accession No. 2001:786400, Order No. 0947-0103, CAS Registry No. 313237-92-2.

Chemcats, "5-Thiazolecarboxylic acid, 4-methyl-2-((phenylsulfonyl)amino)-, ethyl ester," Pharma Library Collection, (May 14, 2001). Chemcats Accession No. 2001:2446055, Order No. NS44365, CAS Registry No. 313237-91-1.

(Continued)

*Primary Examiner*—Kamal A. Saeed
*Assistant Examiner*—Rebecca Anderson
(74) *Attorney, Agent, or Firm*—Foley & Lardner LLP

(57) ABSTRACT

The present invention relates to compounds with the formula (I)

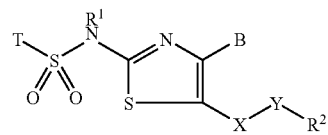

and also to pharmaceutical compositions comprising the compounds, as well as to the use of the compounds in medicine and for the preparation of a medicament which acts on the human 11-β-hydroxysteroid dehydrogenase type 1 enzyme.

4 Claims, No Drawings

OTHER PUBLICATIONS

Chemcats, "5-Thiazolecarboxylic acid, 4-methyl-2-((2-naphthalenylsufonyl)amino)-, ethyl ester," Pharma Library Collection, (May 14, 2001). Chemcats Accession No. 2001:19110, Order No. NS41694, CAS Registry No. 312915-27-8.

Chemcats, "5-Thiazolecarboxylic acid, 4-methyl-2-((4-methylphenyl)sulfonyl)amino)-, ethyl ester," Compounds for Screening, (Jul. 1, 2001). Chemcats Accession No. 2001:1499370, Order No. AG-690/36005052, CAS Registry No. 313230-18-1.

Chemcats, "5-Thiazolecarboxylic acid, 2-(((2-chlorophenyl)sulfonyl)amino)-4-methyl-ethyl ester," Interbioscreen Compound Library, (Feb. 11, 2002). Chemcats Accession No. 2002:175108, Order No. STOCK2S-28380, CAS Registry No. 378764-18-2.

Chemcats, "5-Thiazolecarboxamide, 4-methyl-N-phenyl-2-((phenylsulfonyl)amino)-," Interbioscreen Compound Library, (Feb. 11, 2002). Chemcats Accession No. 2002:174900. Order No. STOCK2S-27987, CAS Registry No. 378768-75-3.

Chemcats, "5-Thiazolecarboxamide, 2-(((2,5-dimethylphenyl)sulfonyl)amino)-4-methyl-N-phenyl-," Interbioscreen Compound Library, (Feb. 11, 2002). Chemcats Accession No. 2002:310940, Order No. STOCK2S-37273, CAS Registry No. 380584-86-1.

Chemcats, "5-Thiazolecarboxamide, 4-methyl-2-(((4-methylphenyl)sulfonyl)amino)-N-phenyl-," Interbioscreen Compound Library, (Feb. 11, 2002). Chemcats Accession No. 2002:310143, Order No. STOCK2S-35716, CAS Registry No. 380590-91-0.

Chemcats, "5-Thiazolecarboxylic acid, 2-(((2,5-dimethylphenyl)sulfonyl)amino)-4-methyl-, ethyl ester," Interbioscreen Compound Library, (Feb. 11, 2002). Chemcats Accession No. 2002:312516, Order No. STOCK2S-40385, CAS Registry No. 380878-60-4.

Anton-Fox et al., "Pharmacological Studies of the Two New Hypoglycaemic Compounds 4-(3-Methyl-5-oxo-2-pyrazolin-1-hl)benzoic Acid and 1-(Mesitylen-2-sulfonyl)-1H-1,2,4-triazole," Arzneim.-Forsch./Drug Res 1994, 44(11), No. 7, pp. 821-826.

Merck & Co. Inc., USA, 1999, Monograph No. 4488, "Glybuzole," CAS Registry No. 1492-02-0.

Hisamitsu Pharmaceutical Oc: "Preparation of 2-(substituted amino)thiazole derivatives as esterase inhibitors," CAPLUS Accession No. 1995:818696, 1995, Document No. 123:228174.

Hisamitsu Pharmaceutical Co: "Preparation of 2-aminothiazole derivatives as esterase inhibitors," CAPLUS Accession No. 1995:867676, 1995, Document No. 123:256699.

Susan Budavari et al., "The Merck Index, An Encyclopedia of Chemical, Drugs, and Biologicals, Twelfth Edition," No. 9115, 1996, pp. 1529.

Friedrich Boberg et al., "Reaction of thioxo compounds with N-chloramidines. VI. Reaction of thioquinolone, dihydrothiazolethione and dihydroisothiazole thione with sodium N-chlorobenzenesulfonamides," CAPLUS Accession No. 1996:420288, 1996, Document No. 125:195596.

CHEMCATS Accession No. 1998:584450, Maybridge, Apr. 3, 2000, 1998.

CHEMCATS Accession No. 1998:584451, Maybridge, Apr. 3, 2000, 1998.

Asahi Chemical Ind: "Therapeutics for Alzheimer's disease containing N-(5-nitro-2-thiazoly)benzenesulfonamides," CAPLUS Accession No. 1996:111694, Document No. 124:165271, 1996.

Hisamitsu Pharmaceutical Co: "Preparation of diphenylthiazoles as pharmaceuticals," CAPLUS Accession No. 1991:680016, Document No. 115:280016, 1991.

Zaki El-Hewehi et al., << Sulfonic acid derivatives: preparation and applicability as mothproofing agents, >> Chemical Abstracts, vol. 58, The Abstract No. 5671, J. Prakt. Chem., 1962, pp. 297-336.

AsInEx Compound Collection, "5-Thiazolecarboxylic acid, 4-methyl-2-(((4-methylphenyl)sulfonyl)amino)-, ethyl ester," CHEMCATS Accession No. 2001:67657, 2001.

Pharma Library Collection, "5-Thiazolecarboxylic acid, 2-(((4-chlorophenyl)sulfonyl)amino)-4-methyl-, ethyl ester," CHEMCATS Accession No. 2001:19109, 2001.

ChemDiv, Inc. Product Library, Apr. 26, 2001, "5-Thiazolecarboxylic acid, 4-methyl-2-(((4-methylphenyl)sulfony)amino-), ethyl ester," CHEMCATS Accession No. 2001:444469, 2001.

V.V. Berezhinskaya, "hypoglycemic activity in relation to chem. Structure of potential oral antidiabetic substances—(I) 1-sulfonyl-3-alkyluread, (II) analogs of 1-sulfonyl-3-alkylureas, (III) 2-benzene-sulfonamido-5-alkyl-1,3,4-thiadiazole and-oxadiazoles," CAOLD Accession No. CA57:3567g, 1962.

Hans Wojahn, "Bromination of sulfapyrimidine and sulfathiazole compounds. II.," Chemical Abstracts, vol. 51, The Abstract No. 6646d, Arch. Pharm., 1955, pp. 288, 321-336.

V.A. Krasovskii et al., << Alkylation of aminothiazoles. VII. Alkylation of 2-aminothiazole and 4-methyl-2-aminothiazole by tert-butyl alcohol, CAPLUS Accession No. 1969:115051, Document No. 70:115051, 1969.

J.D. McColl et al., Effect of Some Sulfonylurea Derivatrives in Experimental Ulcer Formation in the Rat, >> Chemical Abstracts, vol. 59, The Abstract No. 3231, Arch. Intern. Pharmacodyn, 1963, pp. 181-189.

Gaile E. Gudriniece et al., <<Heterocyclic compounds based on diketones. II. 2'-Amino-5,5-dimethyl-1-cyclohexanone(2,3:4',5')thiazole. I., Chemical Abstracts, vol. 59, The Abstract No. 6380, 1962.

Kim, C.H. et al., J. Endocrinol, 1999, vol. 162, pp. 371-379.

C.G. Bellows et al., Bone, 1998, vol. 23, pp. 119-125.

M.S. Cooper et al., Bone, 2000, vol. 27, pp. 375-381.

Hökfelt, Bernt "Hypoglycemic Activity in Relation to Chemical Structure of Potential Oral Antidiabetic Substances. I. 1-Sulfonyl-3-alkylureas," *Journal of Medicinal and Pharmaceutical Chemistry*, 5(1):231-257 (Jan. 6, 1962) ©American Chemical Society.

Sonino et al., "Ketoconazole treatment in Cushing's syndrome: experience in 34 patients," *Clinical Endocrinology* 35:347-352 (1991) ©Blackwell Scientific Publications Ltd.

Verhelst et al., "Use of ketoconazole in the treatment of a virilizing adrenocortical carcinoma," *Acta Endocrinologica* 121:229-234 (1989) ©Acta Endocrinologica (Copenhagen).

Beuchet, Eur. J. Med. Chem., 34(9), p. 773 (1999).

Desai et al., "Sulfonamides. II. Preparation of N1-heterocyclic substituted sulfonamides from alpha-naphthylamine and evaluation of their antibacterial properties," J. Indian Chem. Soc. 46(2):115-18, (1969). CAPLUS accession No. 1969:412872, document No. 71:12872.

Desai et al., "Sulfonamides. IV. Some N-6-heterocyclic sulfonamides from 2-paphthylamine as possible antibacterial agents," J. Indian Chem.. Soc. 46(2):411-14, 1969. CAPLUS accession No. 1969:449825, document No. 71:49825.

Gagiu et al., "Mitodepressive substances. 6. 4-[(Haloacetyl)amino]-N1-R-benzenesulfonamides," Pharmazie 27(3):166, 1972. CAPLUS accession No. 1972:428762, document No. 77:28762.

Di Carlo et al., "Pentobarbital action on the binding capability of methylenoxytetracycline sulfaethylthiazole, and cyanocobalamin with serum macromolecules," Atti Soc. Ital. Sci. Vet. 20:278-82, 1966. CAPLUS accession No. 1967:402061, document No. 67:2061.

Chaurasia et al., "Synthesis of some new 2-sulphanilamidothiazoles as potential fungicides," Agric. Biol. Chem. 45(5):1129-34, 1981. CAPLUS accession No. 1981:480840, document No. 95:80840.

INHIBITORS OF 11-BETA-HYDROXY STEROID DEHYDROGENASE TYPE 1

RELATED APPLICATIONS

This application claims priority to Swedish application number 0103911-4, filed on Nov. 22, 2001, and U.S. provisional application No. 60/348,617, filed on Jan. 14, 2002, the contents of which are incorporated herein by reference.

TECHNICAL FIELD

The present invention relates to novel compounds, to pharmaceutical compositions comprising the compounds, as well as to the use of the compounds in medicine and for the preparation of a medicament which acts on the human 11-β-hydroxysteroid dehydrogenase type 1 enzyme (11βHSD1).

BACKGROUND

1. Glucorticoids, Diabetes and Hepatic Glucose Production

It has been known for more than half a century that glucocorticoids have a central role in diabetes, e.g. the removal of the pituitary or the adrenal gland from a diabetic animal alleviates the most severe symptoms of diabetes and lowers the concentration of glucose in the blood (Long, C. D. and F. D. W. Leukins (1936) J. Exp. Med. 63: 465–490; Houssay, B. A. (1942) Endocrinology 30: 884–892). It is also well established that glucocorticoids enable the effect of glucagon on the liver.

The role of 11βHSD1 as an important regulator of local glucocorticoid effect and thus of hepatic glucose production is well substantiated (see e.g. Jamieson et al. (2000) J. Endocrinol. 165: p. 685–692). The hepatic insulin sensitivity was improved in healthy human volunteers treated with the non-specific 11βHSD1 inhibitor carbenoxolone (Walker, B. R. et al. (1995) J. Clin. Endocrinol. Metab. 80: 3155–3159). Furthermore, the expected mechanism has been established by different experiments with mice and rats. These studies showed that the mRNA levels and activities of two key enzymes in hepatic glucose production were reduced, namely: the rate-limiting enzyme in gluconeogenesis, phosphoenolpyruvate carboxykinase (PEPCK), and glucose-6-phosphatase (G6Pase) catalyzing the last common step of gluconeogenesis and glycogenolysis. Finally, the blood glucose level and hepatic glucose production is reduced in mice having the 11βHSD1 gene knocked-out. Data from this model also confirm that inhibition of 11βHSD1 will not cause hypoglycemia, as predicted since the basal levels of PEPCK and G6Pase are regulated independently of glucocorticoids (Kotelevtsev, Y. et al., (1997) Proc. Natl. Acad. Sci. USA 94: 14924–14929).

FR 2,384,498 discloses compounds having a high hypoglycemic effect. Therefore, treatment of hyperglycemia with these compounds may lead to hypoglycemia.

2. Possible Reduction of Obesity and Obesity Related Cardiovascular Risk Factors Obesity is an important factor in syndrome X as well as in the majority (>80%) of type 2 diabetic, and omental fat appears to be of central importance. Abdominal obesity is closely associated with glucose intolerance, hyperinsulinemia, hypertriglyceridemia, and other factors of the so-called syndrome X (e.g. raised blood pressure, decreased levels of HDL and increased levels of VLDL) (Montague & O'Rahilly, Diabetes 49: 883–888, 2000). Inhibition of the enzyme in pre-adipocytes (stromal cells) has been shown to decrease the rate of differentiation into adipocytes. This is predicted to result in diminished expansion (possibly reduction) of the omental fat depot, i.e. reduced central obesity (Bujalska, I. J., S. Kumar, and P. M. Stewart (1997) Lancet 349: 1210–1213).

Inhibition of 11βHSD1 in mature adipocytes is expected to attenuate secretion of the plasminogen activator inhibitor 1 (PAI-1)—an independent cardiovascular risk factor (Halleux, C. M. et al. (1999) J. Clin. Endocrinol. Metab. 84: 4097–4105). Furthermore, there is a clear correlation between glucocorticoid "activity" and cardiovascular risk factore suggesting that a reduction of the glucocorticoid effects would be beneficial (Walker, B. R. et al. (1998) Hypertension 31: 891–895; Fraser, R. et al. (1999) Hypertension 33: 1364–1368).

Adrenalectomy attenuates the effect of fasting to increase both food intake and hypothalamic neuropeptide Y expression. This supports the role of glucocorticoids in promoting food intake and suggests that inhibition of 11βHSD1 in the brain might increase satiety and therefore reduce food intake (Woods, S. C. et al. (1998) Science, 280: 1378–1383).

3. Possible Beneficial Effect on the Pancreas

Inhibition of 11βHSD1 in isolated murine pancreatic β-cells improves the glucose-stimulated insulin secretion (Davani, B. et al. (2000) J. Biol. Chem. 2000 Nov. 10; 275(45): 34841–4). Glucocorticoids were previously known to reduce pancreatic insulin release in vivo (Billaudel, B. and B. C. J. Sutter (1979) Horm. Metab. Res. 11: 555–560). Thus, inhibition of 11βHSD1 is predicted to yield other beneficial effects for diabetes treatment, besides effects on liver and fat.

4. Possible Beneficial Effects on Cognition and Dementia

Stress and glucocorticoids influence cognitive function (de Quervain, D. J. -F., B. Roozendaal, and J. L. McGaugh (1998) Nature 394: 787–790). The enzyme 11βHSD1 controls the level of glucocorticoid action in the brain and thus contributes to neurotoxicity (Rajan, V., C. R. W. Edwards, and J. R. Seckl, J. (1996) Neuroscience 16: 65–70; Seckl, J. R., Front. (2000) Neuroendocrinol. 18: 49–99). Unpublished results indicate significant memory improvement in rats treated with a non-specific 11βHSD1 inhibitor (J. Seckl, personal communication). Based the above and on the known effects of glucocorticoids in the brain, it may also be suggested that inhibiting 11βHSD1 in the brain may result in reduced anxiety (Tronche, F. et al. (1999) Nature Genetics 23: 99–103). Thus, taken together, the hypothesis is that inhibition of 11βHSD1 in the human brain would prevent reactivation of cortisone into cortisol and protect against deleterious glucocorticoid-mediated effects on neuronal survival and other aspects of neuronal function, including cognitive impairment, depression, and increased appetite (previous section).

WO 99/02502 discloses 5HT$_6$ receptor antagonists for the treatment of CNS disorders. Such antagonists of thiazole structure differ from the compounds according to the present invention in that the former have an aryl group in 4-position. Furthermore, nothing is said about the activity on 11βHSD1.

5. Possible Use of Immuno-modulation Using 11βHSD1 Inhibitors

The general perception is that glucocorticoids suppress the immune system. But in fact there is a dynamic interaction between the immune system and the HPA (hypothalamo-pituitary-adrenal) axis (Rook, G. A. W. (1999) Baillièr's Clin. Endocrinol. Metab. 13: 576–581). The balance between the cell-mediated response and humoral responses is modulated by glucocorticoids. A high glucocorticoid activity, such as at a state of stress, is associated with a humoral response. Thus, inhibition of the enzyme 11βHSD1 has been suggested as a means of shifting the response towards a cell-based reaction.

In certain disease states, including tuberculosis, lepra and psoriasis the immune reaction is normaly biased towards a humoral response when in fact the appropriate response would be cell based. Temporal inhibition of 11βHSD1, local or systemic, might be used to push the immune system into the appropriate response (Mason, D. (1991) Immunology Today 12: 57–60; Rook et al., supra).

An analogous use of 11βHSD1 inhibition, in this case temporal, would be to booster the immune response in association with immunization to ensure that a cell based response would be obtained, when desired.

6. Reduction of Intraocular Pressure

Recent data suggest that the levels of the glucocorticoid target receptors and the 11βHSD enzymes determines the susceptibility to glaucoma (Stokes, J. et al. (2000) Invest. Ophthalmol. 41: 1629–1638). Further, inhibition of 11βHSD1 was recently presented as a novel approach to lower the intraocular pressure (Walker E. A. et al, poster P3-698 at the Endocrine society meeting Jun. 12–15, 1999, San Diego). Ingestion of carbenoxolone, a non-specific inhibitor of 11βHSD1, was shown to reduce the intraocular pressure by 20% in normal subjects. In the eye, expression of 11βHSD1 is confined to basal cells of the corneal epithelium and the non-pigmented epitheliailium of the cornea (the site of aqueous production), to ciliary muscle and to the sphincter and dilator muscles of the iris. In contrast, the distant isoenzyme 11βHSD2 is highly expressed in the non-pigmented ciliary epithelium and corneal endothelium. None of the enzymes is found at the trabecular meshwork, the site of drainage. Thus, 11βHSD1 is suggested to have a role in aqueous production, rather than drainage, but it is presently unknown if this is by interfering with activation of the glucocorticoid or the mineralocorticoid receptor, or both.

7. Reduced Osteoporosis

Glucocorticoids have an essential role in skeletal development and function but are detrimental in excess. Glucocorticoid-induced bone loss is derived, at least in part, via inhibition of bone formation, which includes suppression of osteoblast proliferation and collagen synthesis (Kim, C. H., S. L. Cheng, and G. S. Kim (1999) J. Endocrinol. 162: 371–379). The negative effect on bone nodule formation could be blocked by the non-specific inhibitor carbenoxolone suggesting an important role of 11βHSD1 in the glucocorticoid effect (Bellows, C. G., A. Ciaccia, and J. N. M. Heersche, (1998) Bone 23: 119–125). Other data suggest a role of 11βHSD1 in providing sufficiently high levels of active glucocorticoid in osteoclasts, and thus in augmenting bone resorption (Cooper, M. S. et al. (2000) Bone 27: 375–381). Taken together, these different data suggest that inhibition of 11βHSD1 may have beneficial effects against osteoporosis by more than one mechanism working in parallel.

8. Reduction of Hypertension

Bile acids inhibit 11β-hydroxysteroid dehydrogenase type 2. This results in a shift in the overall body balance in favour of cortisol over cortisone, as shown by studying the ratio of the urinary metabolites (Quattropani C, Vogt B, Odermatt A, Dick B, Frey BM, Frey F J. 2001. J Clin Invest. November; 108(9):1299–305. "Reduced activity of 11beta-hydroxysteroid dehydrogenase in patients with cholestasis".). Reducing the activity of 11βHSD1 in the liver by a selective inhibitor is predicted to reverse this imbalance, and acutely counter the symptoms such as hypertension, while awaiting surgical treatment removing the biliary obstruction.

WO 99/65884 discloses carbon substituted aminothiazole inhibitors of cyclin dependent kinases. These compounds may e.g. be used against cancer, inflammation and arthritis. U.S. Pat. No. 5,856,347 discloses an antibacterial preparation or bactericide comprising 2-aminothiazole derivative and/or salt thereof. Further, U.S. Pat. No. 5,403,857 discloses benzenesulfonamide derivatives having 5-lipoxygenase inhibitory activity. Additionally, tetrahydrothiazolo[5,4-c]pyridines are disclosed in: Analgesic tetrahydrothiazolo [5,4-c]pyridines. Fr. Addn. (1969), 18 pp, Addn. to Fr. 1498465. CODEN: FAXXA3; FR 94123 19690704 CAN 72:100685 AN 1970:100685 CAPLUS and 4,5,6,7-Tetrahydrothiazolo[5,4-c]pyridines. Neth. Appl. (1967), 39 pp. CODEN: NAXXAN NL 6610324 19670124 CAN 68:49593, AN 1968: 49593 CAPLUS. However, none of the above disclosures discloses the compounds according to the present invention, or their use for the treatment of diabetes, obesity, glaucoma, osteoporosis, cognitive disorders, immune disorders, depression, and hypertension.

U.S. Pat. Nos. 5,594,021 and 6,030,991 disclose compounds inhibiting the binding of an endothelin peptide to an endothelin receptor. Such compounds of thiazole structure differ from the compounds according to the present invention in that the former are unsubstituted in both 4- and 5-position. Furthermore, nothing is said about the activity on 11βHSD1.

WO 01/54691 discloses thiazole compounds as antimicrobial agents. Only the antibacterial effect of such compounds has been shown in the pharmacological examples. These compounds differ from the compounds according to the present invention in that the former either are unsubstituted in 5-position or have a free amino group in 2-position.

U.S. Pat. No. 5,783,597 discloses thiophene derivatives as inhibitors of $PGE_2$ and $LTB_4$. Nothing is said about the activity on 11βHSD1.

Consequently, there is a need of new compounds that are useful in the treatment of diabetes, obesity, glaucoma, osteoporosis, cognitive disorders, immune disorders, depression, and hypertension.

SUMMARY OF THE INVENTION

The compounds according to the present invention solves the above problems and embraces a novel class of compounds which has been developed and which inhibit the human 11-β-hydroxysteroid dehydrogenase type 1 enzyme (11-β-$HSD_1$), and may therefore be of use in the treating disorders such as diabetes, obesity, glaucoma, osteoporosis, cognitive disorders, immune disorders, and hypertension.

One object of the present invention is a compound of formula (I)

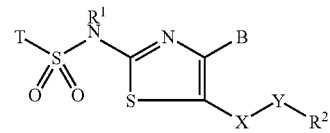

wherein

T is an aryl ring or heteroaryl ring, optionally independently substituted by $[R]_n$, wherein n is an integer 0–5, and R is hydrogen, aryl, heteroaryl, a heterocyclic ring, optionally halogenated $C_{1-6}$-alkyl, optionally halogenated $C_{1-6}$- alkoxy, C$_{1-6}$-alkylsulfonyl, carboxy, cyano, nitro, halogen, aryloxy, arylsulfonyl, arylamino, wherein aryl, heteroaryl and aryloxy residues and heterocyclic rings can further be optionally substituted in one or more positions independently of each other by C$_{1-6}$-acyl, C$_{1-6}$-alkylthio, cyano, nitro, hydrogen, halogen, optionally halogenated C$_{1-6}$-alkyl, optionally halogenated C$_{1-6}$-alkoxy, amide which is optionally mono- or di-substituted, (benzoylamino)methyl, carboxy, 2-thienylmethylamino or ({[4-(2-ethoxy-2-oxoethyl)-1,3-thiazol-2-yl]amino}carbonyl); or T is selected from 5-(dimethylamino)-1-naphthyl and phenyl substituted with one or more of benzeneamino, benzylamino, 3-pyridylmethylamino and 2-thienylmethylamino;

R$^1$ is hydrogen or C$_{1-6}$-alkyl;

X is CH$_2$ or CO;

Y is CH$_2$, CO or a single bond;

B is hydrogen, C$_{1-6}$-alkyl or dimethylaminomethyl;

R$^2$ is selected from C$_{1-6}$-alkyl, azido, arylthio, heteroarylthio, halogen, hydroxymethyl, 2-hydroxyethylaminomethyl, methylsulfonyloxymethyl, 3-oxo-4-morpholinolinylmethylene, C$_{1-6}$-alkoxycarbonyl, 5-methyl-1,3,4-oxadiazol-2-yl;

NR$^3$R$^4$, wherein R$^3$ and R$^4$ are each independently selected from hydrogen, ethyl, isopropyl, n-propyl, optionally halogenated C$_{1-6}$-alkylsulfonyl, C$_{1-6}$-alkoxy, 2-methoxyethyl, 2-hydroxyethyl, 1-methylimidazolylsulfonyl, C$_{1-6}$-acyl, cyclohexylmethyl, cyclopropanecarbonyl, aryl, optionally halogenated arylsulfonyl, furylcarbonyl, tetrahydro-2-furanylmethyl, N-carbethoxypiperidyl, or C$_{1-6}$-alkyl substituted with one or more aryl, heterocyclic or heteroaryl, or NR$^3$R$^4$ represent together heterocyclic systems which can be imidazole, piperidine, pyrrolidine, piperazine, morpholine, oxazepine, oxazole, thiomorpholine, 1,1-dioxidothiomorpholine, 2-(3,4-dihydro-2(1H)isoquinolinyl), (1S,4S)-2-oxa-5-azabicyclo[2.2.1]hept-5-yl, which heterocyclic systems can be optionally substituted by C$_{1-6}$-alkyl, C$_{1-6}$-acyl, hydroxy, oxo, t-butoxycarbonyl;

OCONR$^3$R$^4$, wherein R$^3$ and R$^4$ are each independently selected from hydrogen, C$_{1-6}$-alkyl or form together with the N-atom to which they are attached morpholinyl;

R$^5$O, wherein R$^5$ is hydrogen, optionally halogenated C$_{1-6}$-alkyl, aryl, heteroaryl, C$_{1-6}$-acyl, C$_{1-6}$-alkylsulfonyl, arylcarbonyl, heteroarylcarbonyl, 2-carbomethoxyphenyl;

or a salt, hydrate or solvate thereof;

with the proviso that when:

X is CH$_2$, Y is CH$_2$, then R$^2$ is not methyl, ethyl, diethylamino, 1-pyrrolidinyl, and 1-piperidinyl;

X is CH$_2$, Y is CH$_2$, R$^2$ is morpholinyl, then T is not 4-methylphenyl;

X is CH$_2$, Y is CO, then R$^2$ is not hydroxy;

X is CH$_2$, Y is a single bond, then R$^2$ is not ethyl, n-propyl;

X is CH$_2$, Y is a single bond, R$^2$ is methyl, B is methyl, then T is not 3-chloro-2-methylphenyl;

X is CO, Y is a single bond, then R$^2$ is not methyl;

X is CO, Y is a single bond, R$^2$ is ethoxy, B is methyl, then T is not 3-chloro-2-methylphenyl, 1,1'-biphenyl-4-yl, 4-n-propylphenyl, 2,4-dichloro-6-methylphenyl, and 2,4,6-trichlorophenyl.

It is preferred that:

T is selected from 5-chloro-1,3-dimethyl-1H-pyrazol-4-yl; 4-chloro-2,3,1-benzoxadiazolyl; 5-(dimethylamino)-1-naphthyl; 1-methylimidazol-4-yl; 1-naphthyl; 2-naphthyl; 8-quinolinyl;

thienyl substituted with one or more of (benzoylamino)methyl, bromo, chloro, 3-isoxazolyl, 2-(methylsulfanyl)-4-pyrimidinyl, 1-methyl-5-(trifluoromethyl)pyrazol-3-yl, phenylsulfonyl, pyridyl;

phenyl substituted with one or more of 3-acetylaminophenyl, 3-acetylphenyl, benzeneamino, 1,3-benzodioxol-5-yl, 2-benzofuryl, benzylamino, 3,5-bis(trifluoromethyl)phenyl, bromo, butoxy, carboxy, chloro, 4-carboxyphenyl, 3-chloro-2-cyanophenoxy, 4-chlorophenyl, 5-chloro-2-thienyl, cyano, 3,4-dichlorophenyl, ({[4-(2-ethoxy-2-oxoethyl)-1,3-thiazol-2-yl]amino}carbonyl), fluoro, 5-fluoro-2-methoxyphenyl, 2-furyl, hydrogen, iodo, isopropyl, methanesulfonyl, methoxy, methyl, 4-methyl-1-piperazinyl, 4-methyl-1-piperidinyl, 4-methylsulfanylphenyl, 5-methyl-2-thienyl, 4-morpholinyl, nitro, 3-nitrophenyl, phenoxy, phenyl, n-propyl, 4-pyridyl, 3-pyridylmethylamino, 1-pyrrolidinyl, 2-thienyl, 3-thienyl, 2-thienylmethylamino, trifluoromethoxy, 4-trifluoromethoxyphenyl, trifluoromethyl; or R$^1$ is hydrogen or methyl;

X is CH$_2$ or CO;

Y is CH$_2$, CO or a single bond;

B is hydrogen, methyl or dimethylaminomethyl;

R$^2$ is selected from n-propyl, azido, bromo, chloro, 2-pyridinylsulfanyl, 3-oxo-4-morpholinolinylmethylene, ethoxycarbonyl, 5-methyl-1,3,4-oxadiazol-2-yl, hydroxymethyl, 2-hydroxyethylaminomethyl, methylsulfonyloxymethyl;

NR$^3$R$^4$, wherein R$^3$ and R$^4$ are each independently selected from acetyl, benzhydryl, 1,3-benzodioxol-5-ylmethyl, benzyl, 3-chloro-2-methylphenylsulfonyl, cyclohexyl, cyclohexylmethyl, cyclopropanecarbonyl, ethyl, 2-furylcarbonyl, 2-furylmethyl, hydrogen, 2-hydroxyethyl, 2-(1H-indol-3-yl)ethyl, isopropyl, methoxy, 2-methoxyethyl, 4-(1-methylimidazolyl)sulfonyl, methylsulfonyl, phenyl, (1S)-phenylethyl, n-propyl, tetrahydro-2-furanylmethyl, trifluoromethylsulfonyl, N-carbethoxypiperidyl; or NR$^3$R$^4$ represent together 4-acetylpiperazinyl, 4-t-butoxycarbonylpiperazinyl, 2-(3,4-dihydro-2(1H)isoquinolinyl), (2R,6S)-2,6-dimethylmorpholinyl, (2R)-2,4-dimethyl-1-piperazinyl, 2-hydroxy-3-oxomorpholinyl, imidazolyl, 2-methyl-3-oxomorpholinyl, 4-methyl-2-oxopiperazinyl, 4-methylpiperazinyl, morpholinyl, (1S,4S)-2-oxa-5-aza-bicyclo[2.2.1]hept-5-yl, 2-oxoimidazolinyl, 3-oxomorpholinyl, 3-oxo-1,4-oxazepinyl, 2-oxooxazolinyl, piperazinyl; piperidinyl; pyrrolidinyl; pyrrolidonyl; thiomorpholinyl; 1,1-dioxido-thiomorpholinyl;

OCONR$^3$R$^4$, wherein R$^3$ and R$^4$ are each independently selected from ethyl, hydrogen or form together with the N-atom to which they are attached morpholinyl;

R$^5$O, wherein R$^5$ is acetyl, benzoyl, benzyl, ethyl, 2-fluoroethyl, 2-furylcarbonyl, hydrogen, isobutyryl, isopropyl, methyl, 2-carbomethoxyphenyl, methylsulfonyl, phenyl, n-propionyl, 3-pyridinyl, 2,2,2-trifluoroethyl;

with the proviso that when:

X is CH$_2$, Y is CH$_2$, then R$^2$ is not diethylamino, 1-pyrrolidinyl, and 1-piperidinyl;

X is CH$_2$, Y is CH$_2$, R$^2$ is morpholinyl, then T is not 4-methylphenyl;

X is CH$_2$, Y is CO, then R$^2$ is not hydroxy;

X is CH$_2$, Y is a single bond, then R$^2$ is not n-propyl;

X is CO, Y is a single bond, R$^2$ is ethoxy, B is methyl, then T is not 3-chloro-2-methylphenyl, 1,1'-biphenyl-4-yl, 4-n-propylphenyl, 2,4-dichloro-6-methylphenyl, and 2,4,6-trichlorophenyl.

When X is CH$_2$ and Y is CH$_2$, then it is preferred that:

R$^2$ is selected from n-propyl, azido, bromo, chloro, 2-pyridinylsulfanyl, 3-oxo-4-morpholinolinylmethylene, ethoxycarbonyl, 5-methyl-1,3,4-oxadiazol-2-yl, hydroxymethyl, 2-hydroxyethylaminomethyl, methylsulfonyloxymethyl;

$NR^3R^4$, wherein:
(i) $R^3$ and $R^4$ are either each independently selected from acetyl, benzhydryl, 1,3-benzodioxol-5-ylmethyl, benzyl, 3-chloro-2-methylphenylsulfonyl, cyclohexyl, cyclohexylmethyl, cyclopropanecarbonyl, 2-furylcarbonyl, 2-furylmethyl, hydrogen, 2-hydroxyethyl, 2-(1H-indol-3-yl)ethyl, isopropyl, methoxy, 2-methoxyethyl, methyl, 4-(1-methylimidazolyl)sulfonyl, methylsulfonyl, phenyl, (1S)-phenylethyl, n-propyl, tetrahydro-2-furanylmethyl, trifluoromethylsulfonyl, N-carbethoxypiperidyl; or
(ii) $R^3$ is ethyl and $R^4$ is selected from acetyl, benzhydryl, 1,3-benzodioxol-5-ylmethyl, benzyl, 3-chloro-2-methylphenylsulfonyl, cyclohexyl, cyclohexylmethyl, cyclopropanecarbonyl, 2-furylcarbonyl, 2-furylmethyl, hydrogen, 2-hydroxyethyl, 2-(1H-indol-3-yl)ethyl, isopropyl, methoxy, 2-methoxyethyl, methyl, 4-(1-methylimidazolyl)sulfonyl, methylsulfonyl, phenyl, (1S)-phenylethyl, n-propyl, tetrahydro-2-furanylmethyl, trifluoromethylsulfonyl, N-carbethoxypiperidyl;

$NR^3R^4$ represent together 4-acetylpiperazinyl, 4-t-butoxycarbonylpiperazinyl, 2-(3,4-dihydro-2(1H)isoquinolinyl), (2R,6S)-2,6-dimethylmorpholinyl, (2R)-2,4-dimethyl-1-piperazinyl, 2-hydroxy-3-oxomorpholinyl, imidazolyl, 2-methyl-3-oxomorpholinyl, 4methyl-2-oxopiperazinyl, 4-methylpiperazinyl, (1S,4S)-2-oxa-5-aza-bicyclo[2.2.1]hept-5-yl, 2-oxoimidazolinyl, 3-oxomorpholinyl, 3-oxo-1,4-oxazepinyl, 2-oxooxazolinyl, piperazinyl; pyrrolidonyl, thiomorpholinyl; 1,1-dioxido-thiomorpholinyl;

$OCONR^3R^4$, wherein $R^3$ and $R^4$ are each independently selected from ethyl, hydrogen or form together morpholinyl;

$R^5O$, wherein $R^5$ is acetyl, benzoyl, benzyl, ethyl, 2-fluoroethyl, 2-furylcarbonyl, hydrogen, isobutyryl, isopropyl, methyl, 2-carbomethoxyphenyl, methylsulfonyl, phenyl, n-propionyl, 3-pyridinyl, 2,2,2-trifluoroethyl.

When X is $CH_2$, Y is $CH_2$, and $NR^3R^4$ represent together morpholinyl, then it is preferred that T is selected from 5-chloro-1,3-dimethyl-1H-pyrazol-4-yl; 4-chloro-2,3,1-benzoxadiazolyl; 5-(dimethylamino)-1-naphthyl; 1-methylimidazol-4-yl; 1-naphthyl; 2-naphthyl; 8-quinolinyl;

thienyl substituted with one or more of (benzoylamino)methyl, bromo, chloro, 3-isoxazolyl, 2-(methylsulfanyl)-4-pyrimidinyl, 1-methyl-5-(trifluoromethyl)pyrazol-3-yl, phenylsulfonyl, pyridyl;

phenyl substituted with either:
(i) one or more of 3-acetylaminophenyl, 3-acetylphenyl, benzeneamino, 1,3-benzodioxol-5-yl, 2-benzofuryl, benzylamino, 3,5-bis(trifluoromethyl)phenyl, bromo, butoxy, carboxy, chloro, 4-carboxyphenyl, 3-chloro-2-cyanophenoxy, 4-chlorophenyl, 5-chloro-2-thienyl, cyano, 3,4-dichlorophenyl, ({[4-(2-ethoxy-2-oxoethyl)-1,3-thiazol-2-yl]amino}carbonyl), fluoro, 5-fluoro-2-methoxyphenyl, 2-furyl, hydrogen, iodo, isopropyl, methanesulfonyl, methoxy, 4-methyl-1-piperazinyl, 4-methyl-1-piperidinyl, 4-methylsulfanylphenyl, 5-methyl-2-thienyl, 4-morpholinyl, nitro, 3-nitrophenyl, phenoxy, phenyl, n-propyl, 4-pyridyl, 3-pyridylmethylamino, 1-pyrrolidinyl, 2-thienyl, 3-thienyl, 2-thienylmethylamino, trifluoromethoxy, 4-trifluoromethoxyphenyl, trifluoromethyl; or
(ii) one or more of methyl in any of positions 2, 3, 5 or 6.

When X is $CH_2$ and Y is CO, then it is preferred that $R^2$ is selected from n-propyl, azido, bromo, chloro, 2-pyridinylsulfanyl, 3-oxo-4-morpholinolinylmethylene, ethoxycarbonyl, 5-methyl-1,3,4-oxadiazol-2-yl, hydroxymethyl, 2-hydroxyethylaminomethyl, methylsulfonyloxymethyl;

$NR^3R^4$, wherein $R^3$ and $R^4$ are each independently selected from acetyl, benzhydryl, 1,3-benzodioxol-5-ylmethyl, benzyl, 3-chloro-2-methylphenylsulfonyl, cyclohexyl, cyclohexylmethyl, cyclopropanecarbonyl, ethyl, 2-furylcarbonyl, 2-furylmethyl, hydrogen, 2-hydroxyethyl, 2-(1H-indol-3-yl)ethyl, isopropyl, methoxy, 2-methoxyethyl, methyl, 4-(1-methylimidazolyl)sulfonyl, methylsulfonyl, phenyl, (1S)-phenylethyl, n-propyl, tetrahydro-2-furanylmethyl, trifluoromethylsulfonyl, N-carbethoxypiperidyl; or $NR^3R^4$ represent together 4-acetylpiperazinyl, 4-t-butoxycarbonylpiperazinyl, 2-(3,4-dihydro-2(1H)isoquinolinyl), (2R,6S)-2,6-dimethylmorpholinyl, (2R)-2,4-dimethyl-1-piperazinyl, 2-hydroxy-3-oxomorpholinyl, imidazolyl, 2-methyl-3-oxomorpholinyl, 4-methyl-2-oxopiperazinyl, 4-methylpiperazinyl, morpholinyl, (1S,4S)-2-oxa-5-aza-bicyclo[2.2.1]hept-5-yl, 2-oxoimidazolinyl, 3-oxomorpholinyl, 3-oxo-1,4-oxazepinyl, 2-oxooxazolinyl, piperazinyl; piperidinyl; pyrrolidinyl; pyrrolidonyl, thiomorpholinyl; 1,1-dioxido-thiomorpholinyl;

$OCONR^3R^4$, wherein $R^3$ and $R^4$ are each independently selected from ethyl, hydrogen or form together with the N-atom to which they are attached morpholinyl;

$R^5O$, wherein $R^5$ is acetyl, benzoyl, benzyl, ethyl, 2-fluoroethyl, 2-furylcarbonyl, isobutyryl, isopropyl, methyl, 2-carbomethoxyphenyl, methylsulfonyl, phenyl, n-propionyl, 3-pyridinyl, 2,2,2-trifluoroethyl.

When X is $CH_2$ and Y is a single bond, then it is preferred that $R^2$ is selected from azido, bromo, chloro, 2-pyridinylsulfanyl, 3-oxo-4-morpholinolinylmethylene, ethoxycarbonyl, 5-methyl-1,3,4-oxadiazol-2-yl, hydroxymethyl, 2-hydroxyethylaminomethyl, methylsulfonyloxymethyl;

$NR^3R^4$, wherein $R^3$ and $R^4$ are each independently selected from acetyl, benzhydryl, 1,3-benzodioxol-5-ylmethyl, benzyl, 3-chloro-2-methylphenylsulfonyl, cyclohexyl, cyclohexylmethyl, cyclopropanecarbonyl, ethyl, 2-furylcarbonyl, 2-furylmethyl, hydrogen, 2-hydroxyethyl, 2-(1H-indol-3-yl)ethyl, isopropyl, methoxy, 2-methoxyethyl, methyl, 4-(1-methylimidazolyl)sulfonyl, methylsulfonyl, phenyl, (1S)-phenylethyl, n-propyl, tetrahydro-2-furanylmethyl, trifluoromethylsulfonyl, N-carbethoxypiperidyl; or $NR^3R^4$ represent together 4-acetylpiperazinyl, 4-t-butoxycarbonylpiperazinyl, 2-(3,4-dihydro-2(1H)isoquinolinyl), (2R,6S)-2,6-dimethylmorpholinyl, (2R)-2,4-dimethyl-1-piperazinyl, 2-hydroxy-3-oxomorpholinyl, imidazolyl, 2-methyl-3-oxomorpholinyl, 4-methyl-2-oxopiperazinyl, 4-methylpiperazinyl, morpholinyl, (1S,4S)-2-oxa-5-aza-bicyclo[2.2.1]hept-5-yl, 2-oxoimidazolinyl, 3-oxomorpholinyl, 3-oxo-1,4-oxazepinyl, 2-oxooxazolinyl, piperazinyl; piperidinyl; pyrrolidinyl; pyrrolidonyl, thiomorpholinyl; 1,1-dioxido-thiomorpholinyl;

$OCONR^3R^4$, wherein $R^3$ and $R^4$ are each independently selected from ethyl, hydrogen or form together with the N-atom to which they are attached morpholinyl;

$R^5O$, wherein $R^5$ is acetyl, benzoyl, benzyl, ethyl, 2-fluoroethyl, 2-furylcarbonyl, hydrogen, isobutyryl, isopropyl, methyl, 2-carbomethoxyphenyl, methylsulfonyl, phenyl, n-propionyl, 3-pyridinyl, 2,2,2-trifluoroethyl.

When X is $CH_2$, Y is a single bond, $R^2$ is methyl and B is methyl, then it is preferred that T is selected from 5-chloro-1,3-dimethyl-1H-pyrazol-4-yl; 4-chloro-2,3,1-benzoxadiazolyl; 5-(dimethylamino)-1-naphthyl; 1-methylimidazol-4-yl; 1-naphthyl; 2-naphthyl; 8-quinolinyl;

thienyl substituted with one or more of (benzoylamino)methyl, bromo, chloro, 3-isoxazolyl, 2-(methylsulfanyl)-4- pyrimidinyl, 1-methyl-5-(trifluoromethyl)pyrazol-3-yl, phenylsulfonyl, pyridyl;
  phenyl substituted with either:
  (i) one or more of 3-acetylaminophenyl, 3-acetylphenyl, benzeneamino, 1,3-benzodioxol-5-yl, 2-benzofuryl, benzylamino, 3,5-bis(trifluoromethyl)phenyl, bromo, butoxy, carboxy, 4-carboxyphenyl, 3-chloro-2-cyanophenoxy, 4-chlorophenyl, 5-chloro-2-thienyl, cyano, 3,4-dichlorophenyl, ({[4-(2-ethoxy-2-oxoethyl)-1,3-thiazol-2-yl]amino}carbonyl), fluoro, 5-fluoro-2-methoxyphenyl, 2-furyl, hydrogen, iodo, isopropyl, methanesulfonyl, methoxy, methyl, 4-methyl-1-piperazinyl, 4-methyl-1-piperidinyl, 4-methylsulfanylphenyl, 5-methyl-2-thienyl, 4-morpholinyl, nitro, 3-nitrophenyl, phenoxy, phenyl, n-propyl, 4-pyridyl, 3-pyridylmethylamino, 1-pyrrolidinyl, 2-thienyl, 3-thienyl, 2-thienylmethylamino, trifluoromethoxy, 4-trifluoromethoxyphenyl, trifluoromethyl; or
  (ii) one or more of 3-acetylaminophenyl, 3-acetylphenyl, benzeneamino, 1,3-benzodioxol-5-yl, 2-benzofuryl, benzylamino, 3,5-bis(trifluoromethyl)phenyl, bromo, butoxy, carboxy, chloro, 4-carboxyphenyl, 3-chloro-2-cyanophenoxy, 4-chlorophenyl, 5-chloro-2-thienyl, cyano, 3,4-dichlorophenyl, ({[4-(2-ethoxy-2-oxoethyl)-1,3-thiazol-2-yl]amino}carbonyl), fluoro, 5-fluoro-2-methoxyphenyl, 2-furyl, hydrogen, iodo, isopropyl, methanesulfonyl, methoxy, 4-methyl-1-piperazinyl, 4-methyl-1-piperidinyl, 4-methylsulfanylphenyl, 5-methyl-2-thienyl, 4-morpholinyl, nitro, 3-nitrophenyl, phenoxy, phenyl, n-propyl, 4-pyridyl, 3-pyridylmethylamino, 1-pyrrolidinyl, 2-thienyl, 3-thienyl, 2-thienylmethylamino, trifluoromethoxy, 4-trifluoromethoxyphenyl, trifluoromethyl; or
  (iii) one or more chloro and, in positions 3, 4, 5, one or more methyl.

When X is CO and Y is a single bond, then it is preferred that $R^2$ is selected from n-propyl, azido, bromo, chloro, 2-pyridinylsulfanyl, 3-oxo-4-morpholinolinylmethylene, ethoxycarbonyl, 5-methyl-1,3,4-oxadiazol-2-yl, hydroxymethyl, 2-hydroxyethylaminomethyl, methylsulfonyloxymethyl;

$NR^3R^4$, wherein $R^3$ and $R^4$ are each independently selected from acetyl, benzhydryl, 1,3-benzodioxol-5-ylmethyl, benzyl, 3-chloro-2-methylphenylsulfonyl, cyclohexyl, cyclohexylmethyl, cyclopropanecarbonyl, ethyl, 2-furylcarbonyl, 2-furylmethyl, hydrogen, 2-hydroxyethyl, 2-(1H-indol-3-yl)ethyl, isopropyl, methoxy, 2-methoxyethyl, methyl, 4-(1-methylimidazolyl)sulfonyl, methylsulfonyl, phenyl, (1S)-phenylethyl, n-propyl, tetrahydro-2furanylmethyl, trifluoromethylsulfonyl, N-carbethoxypiperidyl; or $NR^3R^4$ represent together 4-acetylpiperazinyl, 4-t-butoxycarbonylpiperazinyl, 2-(3,4-dihydro-2(1H)isoquinolinyl), (2R,6S)-2,6-dimethylmorpholinyl, (2R)-2,4-dimethyl-1-piperazinyl, 2-hydroxy-3-oxomorpholinyl, imidazolyl, 2-methyl-3-oxomorpholinyl, 4-methyl-2-oxopiperazinyl, 4-methylpiperazinyl, morpholinyl, (1S,4S)-2-oxa-5-aza-bicyclo[2.2.1]hept-5-yl, 2-oxoimidazolinyl, 3-oxomorpholinyl, 3-oxo-1,4-oxazepinyl, 2-oxooxazolinyl, piperazinyl; piperidinyl; pyrrolidinyl; pyrrolidonyl, thiomorpholinyl; 1,1-dioxido-thiomorpholinyl;

$OCONR^3R^4$, wherein $R^3$ and $R^4$ are each independently selected from ethyl, hydrogen or form together with the N-atom to which they are attached morpholinyl;

$R^5O$, wherein $R^5$ is acetyl, benzoyl, benzyl, ethyl, 2-fluoroethyl, 2-furylcarbonyl, hydrogen, isobutyryl, isopropyl, methyl, 2-carbomethoxyphenyl, methylsulfonyl, phenyl, n-propionyl, 3-pyridinyl, 2,2,2-trifluoroethyl;

When X is CO and Y is a single bond and $R^2$ is ethoxy, then it is preferred that T is selected from 5-chloro-1,3-dimethyl-1H-pyrazol-4-yl; 4-chloro-2,3,1-benzoxadiazolyl; 5-(dimethylamino)-1-naphthyl; 1-methylimidazol-4-yl; 1-naphthyl; 2-naphthyl; 8-quinolinyl;
  thienyl substituted with one or more of (benzoylamino)methyl, bromo, chloro, 3-isoxazolyl, 2-(methylsulfanyl)-4-pyrimidinyl, 1-methyl-5-(trifluoromethyl)pyrazol-3-yl, phenylsulfonyl, pyridyl;
  phenyl substituted with either:
  (i) one or more of 3-acetylaminophenyl, 3-acetylphenyl, benzeneamino, 1,3-benzodioxol-5-yl, 2-benzofuryl, benzylamino, 3,5-bis(trifluoromethyl)phenyl, bromo, butoxy, carboxy, 4-carboxyphenyl, 3-chloro-2-cyanophenoxy, 4-chlorophenyl, 5-chloro-2-thienyl, cyano, 3,4-dichlorophenyl, ({[4-(2-ethoxy-2-oxoethyl)-1,3-thiazol-2-yl]amino}carbonyl), fluoro, 5-fluoro-2-methoxyphenyl, 2-furyl, hydrogen, iodo, isopropyl, methanesulfonyl, methoxy, 4-methyl-1-piperazinyl, 4-methyl-1-piperidinyl, 4-methylsulfanylphenyl, 5-methyl-2-thienyl, 4-morpholinyl, nitro, 3-nitrophenyl, phenoxy, 4-pyridyl, 3-pyridylmethylamino, 1-pyrrolidinyl, 2-thienyl, 3-thienyl, 2-thienylmethylamino, trifluoromethoxy, 4-trifluoromethoxyphenyl, trifluoromethyl;
  (ii) one or more of methyl;
  (iii) one or more of chloro, phenyl and n-propyl in either position, and methyl in any of positions 3, 4 or 5;
  (iv) one or more of n-propyl and phenyl in any of positions 2, 3, 5 or 6.

The following compounds are especially preferred:
ethyl (2-{[(2,4-dichloro-5-methylphenyl)sulfonyl]amino}-1,3-thiazol-5-yl)acetate
ethyl (2-{[(4-chlorophenyl)sulfonyl]amino}-1,3-thiazol-5-yl)acetate
ethyl (2-{[(2,4-difluorophenyl)sulfonyl]amino}-1,3-thiazol-5-yl)acetate
ethyl (2-{[(2,5-dichlorothien-3-yl)sulfonyl]amino}-1,3-thiazol-5-yl)acetate
ethyl (2-{[(2-chlorophenyl)sulfonyl]amino}-1,3-thiazol-5-yl)acetate
ethyl {2-[(1-naphthylsulfonyl)amino]-1,3-thiazol-5-yl}acetate
ethyl (2-{[(3-chloro-2-methylphenyl)sulfonyl]amino}-1,3-thiazol-5-yl)acetate
2-(2-{[(3-chloro-2-methylphenyl)sulfonyl]amino}-1,3-thiazol-5-yl)-N-methylacetamide
2-(2-{[(3-chloro-2-methylphenyl)sulfonyl]amino}-1,3-thiazol-5-yl)-N-ethylacetamide
ethyl {2-[(1,1'-biphenyl-4-ylsulfonyl)amino]-1,3-thiazol-5-yl}acetate
ethyl (2-{[(4-nitrophenyl)sulfonyl]amino}-1,3-thiazol-5-yl)acetate
ethyl (2-{[(4-methoxyphenyl)sulfonyl]amino}-1,3-thiazol-5-yl)acetate
ethyl (2-{[(2,5-dichlorophenyl)sulfonyl]amino}-1,3-thiazol-5-yl)acetate
3-chloro-N-[5-(2-hydroxyethyl)-1,3-thiazol-2-yl]-2-methylbenzenesulfonamide
3-chloro-N-[5-(2-ethoxyethyl)-1,3-thiazol-2-yl]-2-methylbenzenesulfonamide
ethyl (2-{[(3-chlorophenyl)sulfonyl]amino}-1,3-thiazol-5-yl)acetate
ethyl (2-{[(4-fluorophenyl)sulfonyl]amino}-1,3-thiazol-5-yl)acetate
ethyl (2-{[(4-isopropylphenyl)sulfonyl]amino}-1,3-thiazol-5-yl)acetate
ethyl [2-({[4-({[4-(2-ethoxy-2-oxoethyl)-1,3-thiazol-2-yl]amino}carbonyl)phenyl]sulfonyl}amino)-1,3-thiazol-5-yl]acetate 2-(2-{[(3-chloro-2-methylphenyl)sulfonyl]amino}-1,3-thiazol-5-yl)-N,N-diethylacetamide
ethyl [2-({[2-(trifluoromethyl)phenyl]sulfonyl}amino)-1,3-thiazol-5-yl]acetate
ethyl [2-({[3-(trifluoromethyl)phenyl]sulfonyl}amino)-1,3-thiazol-5-yl]acetate
ethyl [2-({[4-(trifluoromethyl)phenyl]sulfonyl}amino)-1,3-thiazol-5-yl]acetate
methyl (2-{[(3-chloro-2-methylphenyl)sulfonyl]amino}-1,3-thiazol-5-yl)acetate (Example 2)
3-chloro-N-[5-(2-isopropoxyethyl)-1,3-thiazol-2-yl]-2-methylbenzenesulfonamide
3-chloro-N-[5-(2-methoxyethyl)-1,3-thiazol-2-yl]-2-methylbenzenesulfonamide
2-(2-{[(3-chloro-2-methylphenyl)sulfonyl]amino}-1,3-thiazol-5-yl)ethyl methanesulfonate
2-(2-{[(3-chloro-2-methylphenyl)sulfonyl]amino}-1,3-thiazol-5-yl)acetamide
3-chloro-N-{5-[2-(2-fluoroethoxy)ethyl]-1,3-thiazol-2-yl}-2-methylbenzenesulfonamide
3-chloro-2-methyl-N-{5-[2-(2,2,2-trifluoroethoxy)ethyl]-1,3-thiazol-2-yl}benzenesulfonamide
2-(2-{[(3-chloro-2-methylphenyl)sulfonyl]amino}-1,3-thiazol-5-yl)ethyl acetate
3-chloro-2-methyl-N-[5-(2-morpholin-4-ylethyl)-1,3-thiazol-2-yl]benzenesulfonamide (Example 1)
N-[5-(2-bromoethyl)-1,3-thiazol-2-yl]-3-chloro-2-methylbenzenesulfonamide
2-(2-{[(3-chloro-2-methylphenyl)sulfonyl]amino}-1,3-thiazol-5-yl)ethyl morpholine-4-carboxylate
2-(2-{[(3-chloro-2-methylphenyl)sulfonyl]amino}-1,3-thiazol-5-yl)ethyl diethylcarbamate
2-(2-{[(3-chloro-2-methylphenyl)sulfonyl]amino}-1,3-thiazol-5-yl)ethyl propionate
2-(2-{[(3-chloro-2-methylphenyl)sulfonyl]amino}-1,3-thiazol-5-yl)ethyl 2-methylpropanoate
2-(2-{[(3-chloro-2-methylphenyl)sulfonyl]amino}-1,3-thiazol-5-yl)ethyl 2-furoate
2-(2-{[(3-chloro-2-methylphenyl)sulfonyl]amino}-1,3-thiazol-5-yl)ethyl benzoate
2-(2-{[(3-chloro-2-methylphenyl)sulfonyl]amino}-1,3-thiazol-5-yl)-N-methoxy-N-methylacetamide
2-(2-{[(3-chloro-2-methylphenyl)sulfonyl]amino}-1,3-thiazol-5-yl)ethyl ethylcarbamate
N-[2-(2-{[(3-chloro-2-methylphenyl)sulfonyl]amino}-1,3-thiazol-5-yl)ethyl]-N-ethylacetamide
3-chloro-2-methyl-N-[5-(2-oxopentyl)-1,3-thiazol-2-yl]benzenesulfonamide
N-{5-[2-(1,1-dioxidothiomorpholin-4-yl)-2-oxoethyl]-1,3-thiazol-2-yl}-4-propylbenzenesulfonamide
2,4-dichloro-6-methyl-N-{5-[2-(4-methylpiperazin-1-yl)-2-oxoethyl]-1,3-thiazol-2-yl}benzenesulfonamide
3-chloro-2-methyl-N-{5-[2-(3-oxomorpholin-4-yl)ethyl]-1,3-thiazol-2-yl}benzenesulfonamide
2,4-dichloro-6-methyl-N-[5-(2-morpholin-4-yl-2-oxoethyl)-1,3-thiazol-2-yl]benzenesulfonamide
N-[5-(2-morpholin-4-yl-2-oxoethyl)-1,3-thiazol-2-yl]-1,1'-biphenyl-4-sulfonamide
N-[5-(2-morpholin-4-yl-2-oxoethyl)-1,3-thiazol-2-yl]-4-propylbenzenesulfonamide
N-[5-(2-oxo-2-thiomorpholin-4-ylethyl)-1,3-thiazol-2-yl]-1,1'-biphenyl-4-sulfonamide
N-[5-(2-oxo-2-thiomorpholin-4-ylethyl)-1,3-thiazol-2-yl]-4-propylbenzenesulfonamide
2,4-dichloro-6-methyl-N-[5-(2-oxo-2-thiomorpholin-4-ylethyl)-1,3-thiazol-2-yl]benzenesulfonamide
N-[5-(2-oxo-2-piperidin-1-ylethyl)-1,3-thiazol-2-yl]-1,1'-biphenyl-4-sulfonamide
N-[5-(2-oxo-2-piperidin-1-ylethyl)-1,3-thiazol-2-yl]-4-propylbenzenesulfonamide
2,4-dichloro-6-methyl-N-[5-(2-oxo-2-piperidin-1-ylethyl)-1,3-thiazol-2-yl]benzenesulfonamide
ethyl oxo(2-{[(4-propylphenyl)sulfonyl]amino}-1,3-thiazol-5-yl)acetate
ethyl (2-{[(3-chloro-2-methylphenyl)sulfonyl]amino}-1,3-thiazol-5-yl)(oxo)acetate
ethyl oxo(2-{[(2,4,6-trichlorophenyl)sulfonyl]amino}-1,3-thiazol-5-yl)acetate
ethyl {2-[(1,1'-biphenyl-4-ylsulfonyl)amino]-1,3-thiazol-5-yl}(oxo)acetate
3-chloro-2-methyl-N-[4-methyl-5-(2-morpholin-4-yl-2-oxoethyl)-1,3-thiazol-2-yl]benzenesulfonamide
2,4,6-trichloro-N-[4-methyl-5-(2-morpholin-4-yl-2-oxoethyl)-1,3-thiazol-2-yl]benzenesulfonamide
2-{2-[(1,1'-biphenyl-4-ylsulfonyl)amino]-1,3-thiazol-5-yl}-N-ethyl-N-methylacetamide
N-ethyl-N-methyl-2-(2-{[(4-propylphenyl)sulfonyl]amino}-1,3-thiazol-5-yl)acetamide
2-(2-{[(2,4-dichloro-6-methylphenyl)sulfonyl]amino}-1,3-thiazol-5-yl)-N-ethyl-N-methylacetamide
N-[4-methyl-5-(2-morpholin-4-yl-2-oxoethyl)-1,3-thiazol-2-yl]-1,1'-biphenyl-4-sulfonamide
2-{2-[(1,1'-biphenyl-4-ylsulfonyl)amino]-1,3-thiazol-5-yl}-N-isopropyl-N-methylacetamide
2-{2-[(1,1'-biphenyl-4-ylsulfonyl)amino]-1,3-thiazol-5-yl}-N,N-diethylacetamide
N,N-diethyl-2-(2-{[(4-propylphenyl)sulfonyl]amino}-1,3-thiazol-5-yl)acetamide
2-(2-{[(2,4-dichloro-6-methylphenyl)sulfonyl]amino}-1,3-thiazol-5-yl)-N,N-diethylacetamide
ethyl (2-{[(4-bromo-5-chlorothien-2-yl)sulfonyl]amino}-1,3-thiazol-5-yl)acetate
ethyl (2-{[(3-bromo-5-chlorothien-2-yl)sulfonyl]amino}-1,3-thiazol-5-yl)acetate
ethyl {2-[({5-[1-methyl-5-(trifluoromethyl)-1H-pyrazol-3-yl]thien-2-yl}sulfonyl)amino]-1,3-thiazol-5-yl}acetate
ethyl {2-[({5-[2-(methylthio)pyrimidin-4-yl]thien-2-yl}sulfonyl)amino]-1,3-thiazol-5-yl}acetate
2-{2-[(1,1'-biphenyl-4-ylsulfonyl)amino]-1,3-thiazol-5-yl}-N,N-diisopropylacetamide
N,N-diisopropyl-2-(2-{[(4-propylphenyl)sulfonyl]amino}-1,3-thiazol-5-yl)acetamide
2-(2-{[(2,4-dichloro-6-methylphenyl)sulfonyl]amino}-1,3-thiazol-5-yl)-N,N-diisopropylacetamide
methyl (4-methyl-2-{[(2,4,6-trichlorophenyl)sulfonyl]amino}-1,3-thiazol-5-yl)acetate
2-(2-{[(3-chloro-2-methylphenyl)sulfonyl]amino}-1,3-thiazol-5-yl)-N,N-dipropylacetamide
3-chloro-2-methyl-N-[5-(2-oxo-2-piperazin-1-ylethyl)-1,3-thiazol-2-yl]benzenesulfonamide
4-bromo-2-methyl-N-[5-(2-morpholin-4-yl-2-oxoethyl)-1,3-thiazol-2-yl]benzenesulfonamide
N-[5-(2-morpholin-4-yl-2-oxoethyl)-1,3-thiazol-2-yl]-2,4-bis(trifluoromethyl)benzenesulfonamide
2-methyl-N-[5-(2-morpholin-4-yl-2-oxoethyl)-1,3-thiazol-2-yl]-4-(trifluoromethoxy)benzenesulfonamide
N-[5-(2-morpholin-4-yl-2-oxoethyl)-1,3-thiazol-2-yl]-4-phenoxybenzenesulfonamide
ethyl (2-{[(2,3,4-trichlorophenyl)sulfonyl]amino}-1,3-thiazol-5-yl)acetate
ethyl (2-{[(4-bromo-2,5-difluorophenyl)sulfonyl]amino}-1,3-thiazol-5-yl)acetate ethyl [2-({[4-(trifluoromethoxy)phenyl]sulfonyl}amino)-1,3-thiazol-5-yl]acetate
ethyl [2-({[4-(phenylsulfonyl)thien-2-yl]sulfonyl}amino)-1,3-thiazol-5-yl]acetate
ethyl [2-({[5-(phenylsulfonyl)thien-2-yl]sulfonyl}amino)-1,3-thiazol-5-yl]acetate
ethyl (2-{[(2,6-dichlorophenyl)sulfonyl]amino}-1,3-thiazol-5-yl)acetate
ethyl (2-{[(2,4-dichlorophenyl)sulfonyl]amino}-1,3-thiazol-5-yl)acetate
tert-butyl 4-[(2-{[(3-chloro-2-methylphenyl)sulfonyl]amino}-1,3-thiazol-5-yl)acetyl]piperazine-1-carboxylate
2-(2-{[(3-chloro-2-methylphenyl)sulfonyl]amino}-1,3-thiazol-5-yl)-N,N-dimethylacetamide
3-chloro-2-methyl-N-{5-[2-(pyridin-3-yloxy)ethyl]-1,3-thiazol-2-yl}benzenesulfonamide
2-(2-{[(3-chloro-2-methylphenyl)sulfonyl]amino}-1,3-thiazol-5-yl)-N-isopropyl-N-methylacetamide
2-(2-{[(3-chloro-2-methylphenyl)sulfonyl]amino}-1,3-thiazol-5-yl)-N-ethyl-N-methylacetamide
3-chloro-2-methyl-N-[5-(2-oxo-2-thiomorpholin-4-yl-ethyl)-1,3-thiazol-2-yl]benzenesulfonamide
ethyl (2-{[(4-bromo-2-fluorophenyl)sulfonyl]amino}-1,3-thiazol-5-yl)acetate
3-chloro-2-methyl-N-[5-(2-morpholin-4-yl-2-oxoethyl)-1,3-thiazol-2-yl]benzenesulfonamide (Example 4)
methyl (2-{[(4-chlorophenyl)sulfonyl]amino}-4-methyl-1,3-thiazol-5-yl)acetate
methyl (2-{[(3-chloro-2-methylphenyl)sulfonyl]amino}-4-methyl-1,3-thiazol-5-yl)acetate
2-(2-{[(3-chloro-2-methylphenyl)sulfonyl]amino}-1,3-thiazol-5-yl)-N,N-diisopropylacetamide (Example 5)
3-chloro-2-methyl-N-[5-(2-oxo-2-pyrrolidin-1-ylethyl)-1,3-thiazol-2-yl]benzenesulfonamide
ethyl (2-{[(3-methoxyphenyl)sulfonyl]amino}-1,3-thiazol-5-yl)acetate
ethyl (2-{[(5-fluoro-2-methylphenyl)sulfonyl]amino}-1,3-thiazol-5-yl)acetate
ethyl (2-{[(4-propylphenyl)sulfonyl]amino}-1,3-thiazol-5-yl)acetate
3-chloro-2-methyl-N-[5-(2-oxo-2-piperidin-1-ylethyl)-1,3-thiazol-2-yl]benzenesulfonamide
ethyl (2-{[(3,5-dichlorophenyl)sulfonyl]amino}-1,3-thiazol-5-yl)acetate
ethyl (2-{[(3,4-dichlorophenyl)sulfonyl]amino}-1,3-thiazol-5-yl)acetate
ethyl (2-{[(2,4-dichloro-6-methylphenyl)sulfonyl]amino}-1,3-thiazol-5-yl)acetate
3-chloro-2-methyl-N-[5-(morpholin-4-ylmethyl)-1,3-thiazol-2-yl]benzenesulfonamide
3-chloro-N-{5-[2-(1H-imidazol-1-yl)ethyl]-1,3-thiazol-2-yl}-2-methylbenzenesulfonamide
N-[2-(2-{[(3-chloro-2-methylphenyl)sulfonyl]amino}-1,3-thiazol-5-yl)ethyl]acetamide
ethyl [2-({[2-methyl-4-(trifluoromethoxy)phenyl]sulfonyl}amino)-1,3-thiazol-5-yl]acetate
ethyl (2-{[(2,3,4-trifluorophenyl)sulfonyl]amino}-1,3-thiazol-5-yl)acetate
ethyl (2-{[(2,4,6-trifluorophenyl)sulfonyl]amino}-1,3-thiazol-5-yl)acetate
3-chloro-2-methyl-N-(5-{2-[(methylsulfonyl)amino]ethyl}-1,3-thiazol-2-yl)benzenesulfonamide
ethyl (2-{[(5-chlorothien-2-yl)sulfonyl]amino}-1,3-thiazol-5-yl)acetate
ethyl (2-{[(2-chloro-4-fluorophenyl)sulfonyl]amino}-1,3-thiazol-5-yl)acetate
ethyl (2-{[(5-isoxazol-3-ylthien-2-yl)sulfonyl]amino}-1,3-thiazol-5-yl)acetate
ethyl (2-{[(4-phenoxyphenyl)sulfonyl]amino}-1,3-thiazol-5-yl)acetate
ethyl [2-({[2,4-bis(trifluoromethyl)phenyl]sulfonyl}amino)-1,3-thiazol-5-yl]acetate
3-chloro-2-methyl-N-{5-[2-(3-oxo-1,4-oxazepan-4-yl)ethyl]-1,3-thiazol-2-yl}benzenesulfonamide
3-chloro-2-methyl-N-{5-[2-(2-oxopyrrolidin-1-yl)ethyl]-1,3-thiazol-2-yl}benzenesulfonamide
3-chloro-2-methyl-N-(5-{2-[methyl(methylsulfonyl)amino]ethyl}-1,3-thiazol-2-yl)benzenesulfonamide
N-[2-(2-{[(3-chloro-2-methylphenyl)sulfonyl]amino}-1,3-thiazol-5-yl)ethyl]-N-methylcyclopropanecarboxamide
3-chloro-2-methyl-N-{5-[2-(4-methyl-2-oxopiperazin-1-yl)ethyl]-1,3-thiazol-2-yl}benzenesulfonamide
3-chloro-2-methyl-N-[5-(2-{[(trifluoromethyl)sulfonyl]amino}ethyl)-1,3-thiazol-2-yl]benzenesulfonamide
2,4-dichloro-N-{5-[2-(3-oxomorpholin-4-yl)ethyl]-1,3-thiazol-2-yl}benzenesulfonamide
2,4-dichloro-6-methyl-N-{5-[2-(3-oxomorpholin-4-yl)ethyl]-1,3-thiazol-2-yl}benzenesulfonamide
4-(2-furyl)-N-[5-(2-morpholin-4-yl-2-oxoethyl)-1,3-thiazol-2-yl]benzenesulfonamide
5'-fluoro-2'-methoxy-N-[5-(2-morpholin-4-yl-2-oxoethyl)-1,3-thiazol-2-yl]-1,1'-biphenyl-4-sulfonamide
4-(5-methylthien-2-yl)-N-[5-(2-morpholin-4-yl-2-oxoethyl)-1,3-thiazol-2-yl]benzenesulfonamide
3'-acetyl-N-[5-(2-morpholin-4-yl-2-oxoethyl)-1,3-thiazol-2-yl]-1,1'-biphenyl-4-sulfonamide
N-[5-(2-morpholin-4-yl-2-oxoethyl)-1,3-thiazol-2-yl]-4'-(trifluoromethoxy)-1,1'-biphenyl-4-sulfonamide
3',4'-dichloro-N-[5-(2-morpholin-4-yl-2-oxoethyl)-1,3-thiazol-2-yl]-1,1'-biphenyl-4-sulfonamide
4-(1,3-benzodioxol-5-yl)-N-[5-(2-morpholin-4-yl-2-oxoethyl)-1,3-thiazol-2-yl]benzenesulfonamide
N-[5-(2-morpholin-4-yl-2-oxoethyl)-1,3-thiazol-2-yl]-4-pyridin-4-ylbenzenesulfonamide
N-[4'-({[5-(2-morpholin-4-yl-2-oxoethyl)-1,3-thiazol-2-yl]amino}sulfonyl)-1,1'-biphenyl-3-yl]acetamide
N-[5-(2-morpholin-4-yl-2-oxoethyl)-1,3-thiazol-2-yl]-4-thien-3-ylbenzenesulfonamide
N-[5-(2-morpholin-4-yl-2-oxoethyl)-1,3-thiazol-2-yl]-4-thien-2-ylbenzenesulfonamide
4'-({[5-(2-morpholin-4-yl-2-oxoethyl)-1,3-thiazol-2-yl]amino}sulfonyl)-1,1'-biphenyl-4-carboxylic acid
4'-(methylthio)-N-[5-(2-morpholin-4-yl-2-oxoethyl)-1,3-thiazol-2-yl]-1,1'-biphenyl-4-sulfonamide
N-[5-(2-morpholin-4-yl-2-oxoethyl)-1,3-thiazol-2-yl]-3',5'-bis(trifluoromethyl)-1,1'-biphenyl-4-sulfonamide
4'-chloro-N-[5-(2-morpholin-4-yl-2-oxoethyl)-1,3-thiazol-2yl]-1,1'-biphenyl-4-sulfonamide
N-[5-(2-morpholin-4-yl-2-oxoethyl)-1,3-thiazol-2-yl]-3'-nitro-1,1'-biphenyl-4-sulfonamide
isopropyl (2-{[(3-chloro-2-methylphenyl)sulfonyl]amino}-1,3-thiazol-5-yl)acetate Another object of the present invention is a compound as described above for medical use.

Another object of the present invention is a method for the treatment or prevention of diabetes, syndrome X, obesity, glaucoma, hyperlipidemia, hyperglycemia, hyperinsulinemia, hypertension, osteoporosis, dementia, depression, virus diseases or inflammatory disorders without causing hypoglycemia and to achieve immuno-modulation, preferably tuberculosis, lepra, and psoriasis, said method comprising administering to a mammal, including a human, in need of such treatment (e.g., identified as in need thereof) an effective amount of a compound of formula (I) or a composition having a compound of formula (I) in it:

wherein

T is an aryl ring or heteroaryl ring, optionally independently substituted by $[R]_n$, wherein n is an integer 0–5, and R is hydrogen, aryl, heteroaryl, a heterocyclic ring, optionally halogenated $C_{1-6}$-alkyl, optionally halogenated $C_{1-6}$-alkoxy, $C_{1-6}$-alkylsulfonyl, carboxy, cyano, nitro, halogen, amine which is optionally mono- or di-substituted, amide which is optionally mono- or di-substituted, aryloxy, arylsulfonyl, arylamino, wherein aryl, heteroaryl and aryloxy residues and heterocyclic rings can further be optionally substituted in one or more positions independently of each other by $C_{1-6}$-acyl, $C_{1-6}$-alkylthio, cyano, nitro, hydrogen, halogen, optionally halogenated $C_{1-6}$-alkyl, optionally halogenated $C_{1-6}$-alkoxy, amide which is optionally mono- or di-substituted, (benzoylamino)methyl, carboxy, 2-thienylmethylamino or ({[4-(2-ethoxy-2-oxoethyl)-1,3-thiazol-2-yl]amino}carbonyl);

$R^1$ is hydrogen or $C_{1-6}$-alkyl;

X is $CH_2$ or CO;

Y is $CH_2$, CO or a single bond;

B is hydrogen, $C_{1-6}$-alkyl or dimethylaminomethyl;

$R^2$ is selected from $C_{1-6}$-alkyl, azido, arylthio, heteroarylthio, halogen, hydroxymethyl, 2-hydroxyethylaminomethyl, methylsulfonyloxymethyl, 3-oxo-4-morpholinolinylmethylene, $C_{1-6}$-alkoxycarbonyl, 5-methyl-1,3,4-oxadiazol-2-yl;

$NR^3R^4$, wherein $R^3$ and $R^4$ are each independently selected from hydrogen, $C_{1-6}$-alkyl, optionally halogenated $C_{1-6}$-alkylsulfonyl, $C_{1-6}$-alkoxy, 2-methoxyethyl, 2-hydroxyethyl, 1-methylimidazolylsulfonyl, $C_{1-6}$-acyl, cyclohexylmethyl, cyclopropanecarbonyl, aryl, optionally halogenated arylsulfonyl, furylcarbonyl, tetrahydro-2-furanylmethyl, N-carbethoxypiperidyl or $C_{1-6}$-alkyl substituted with one or more aryl, heterocyclic or heteroaryl, or $NR^3R^4$ represent together heterocyclic systems which can be imidazole, piperidine, pyrrolidine, piperazine, morpholine, oxazepine, oxazole, thiomorpholine, 1,1-dioxidothiomorpholine, 2-(3,4-dihydro-2(1H)isoquinolinyl), (1S,4S)-2-oxa-5-azabicyclo[2.2.1]hept-5-yl, which heterocyclic systems can be optionally substituted by $C_{1-6}$-alkyl, $C_{1-6}$-acyl, hydroxy, oxo, t-butoxycarbonyl;

$OCONR^3R^4$, wherein $R^3$ and $R^4$ are each independently selected from hydrogen, $C_{1-6}$-alkyl or form together with the N-atom to which they are attached morpholinyl;

$R^5O$, wherein $R^5$ is hydrogen, optionally halogenated $C_{1-6}$-alkyl, aryl, heteroaryl, $C_{1-6}$-acyl, $C_{1-6}$-alkylsulfonyl, arylcarbonyl, heteroarylcarbonyl, 2-carbomethoxyphenyl;

or a salt, hydrate or solvate thereof;

with the proviso that when:

X is $CH_2$, Y is $CH_2$, then $R^2$ is not methyl and ethyl;

X is $CH_2$, Y is a single bond, then $R^2$ is not ethyl and n-propyl;

X is $CH_2$, Y is a single bond, $R^2$ is methyl, B is methyl, then T is not 3-chloro-2-methylphenyl;

X is CO, Y is a single bond, then $R^2$ is not methyl;

X is CO, Y is a single bond, $R^2$ is ethoxy, B is methyl, then T is not 3-chloro-2-methylphenyl, 1,1'-biphenyl-4-yl, 4-n-propylphenyl, 2,4-dichloro-6-methylphenyl, and 2,4,6-trichlorophenyl.

In another aspect, this invention features a method for inhibiting a human 11-β-hydroxysteroid dehydrogenase type 1 enzyme. The method includes administering to a subject (e.g., mammal, human, or animal) in need thereof (e.g., identified as in need thereof) an effective amount of a compound of any of the formulae delineated herein or a composition comprising any of the formulae herein.

The present invention also features a method for treating 11-β-hydroxysteroid dehydrogenase type 1 enzyme-mediated disorders. The method includes administering to a subject (e.g., mammal, human, or animal) in need thereof (e.g., identified as in need thereof) an effective amount of a compound of any of the formulae delineated herein or a composition comprising any of the formulae delineated herein. The 11-β-hydroxysteroid dehydrogenase type 1 enzyme-mediated disorder is any disorder or symptom wherein the 11-β-hydroxysteroid dehydrogenase type 1 enzyme is involved in the process or presentation of the disorder or the symptom. The 11-β-hydroxysteroid dehydrogenase type 1 enzyme-mediated disorders include, but are not limited to, diabetes, syndrome X, obesity, glaucoma, hyperlipidemia, hyperglycemia, hyperinsulinemia, hypertension, osteoporosis, dementia, depression, virus diseases, inflammatory disorders, and immuno-modulation. Preferred examples of immuno-modulation are tuberculosis, lepra, and psoriasis. When the disorder is hyperglycemia, the treatment thereof does not cause hypoglycemia.

The methods delineated herein can also include the step of identifying that the subject is in need of treatment of diseases or disorders described above. The identification can be in the judgment of a subject or a health professional and can be subjective (e.g., opinion) or objective (e.g., measurable by a test or a diagnostic method).

These compounds may also be used in the manufacture of a medicament for the prevention, management or treatment of diabetes, syndrome X, obesity, glaucoma, hyperlipidemia, hyperglycemia, hyperinsulinemia, hypertension, osteoporosis, dementia, depression, virus diseases or inflammatory disorders without causing hypoglycemia and to achieve immuno-modulation. Preferred examples of immuno-modulation are tuberculosis, lepra, and psoriasis.

It is preferred that:

T is selected from 5-chloro-1,3-dimethyl-1H-pyrazol-4-yl; 4-chloro-2,3,1-benzoxadiazolyl; 5-(dimethylamino)-1-naphthyl; 1-methylimidazol-4-yl; 1-naphthyl; 2-naphthyl; 8-quinolinyl;

thienyl substituted with one or more of (benzoylamino)methyl, bromo, chloro, 3-isoxazolyl, 2-(methylsulfanyl)-4-pyrimidinyl, 1-methyl-5-(trifluoromethyl)pyrazol-3-yl, phenylsulfonyl, pyridyl;

phenyl substituted with one or more of acetylamino, 3-acetylaminophenyl, 3-acetylphenyl, benzeneamino, 1,3-benzodioxol-5-yl, 2-benzofuryl, benzylamino, 3,5-bis(trifluoromethyl)phenyl, bromo, butoxy, carboxy, chloro, 4-carboxyphenyl, 3-chloro-2-cyanophenoxy, 4-chlorophenyl, 5-chloro-2-thienyl, cyano, 3,4-dichlorophenyl, ({[4-(2-ethoxy-2-oxoethyl)-1,3-thiazol-2-yl]amino}carbonyl), fluoro, 5-fluoro-2-methoxyphenyl, 2-furyl, hydrogen, iodo, isopropyl, methanesulfonyl, methoxy, methyl, 4-methyl-1-piperazinyl, 4-methyl-1-piperidinyl, 4-methylsulfanylphenyl, 5-methyl-2-thienyl, 4-morpholinyl, nitro, 3-nitrophenyl, phenoxy, phenyl, n-propyl, 4-pyridyl, 3-pyridylmethylamino, 1-pyrrolidinyl, 2-thienyl, 3-thienyl, 2-thienylmethylamino, trifluoromethoxy, 4-trifluoromethoxyphenyl, trifluoromethyl; or $R^1$ is hydrogen or methyl;

X is $CH_2$ or CO;

Y is $CH_2$, CO or a single bond;

B is hydrogen, methyl or dimethylaminomethyl;

$R^2$ is selected from n-propyl, azido, bromo, chloro, 2-pyridinylsulfanyl, 3-oxo-4-morpholinolinylmethylene, ethoxycarbonyl, 5-methyl-1,3,4-oxadiazol-2-yl, hydroxymethyl, 2-hydroxyethylaminomethyl, methylsulfonyloxymethyl;

NR³R⁴, wherein R³ and R⁴ are each independently selected from acetyl, benzhydryl, 1,3-benzodioxol-5-ylmethyl, benzyl, 3-chloro-2-methylphenylsulfonyl, cyclohexyl, cyclohexylmethyl, cyclopropanecarbonyl, ethyl, 2-furylcarbonyl, 2-furylmethyl, hydrogen, 2-hydroxyethyl, 2-(1H-indol-3-yl)ethyl, isopropyl, methoxy, 2-methoxyethyl, methyl, 4-(1-methylimidazolyl)sulfonyl, methylsulfonyl, phenyl, (1S)-phenylethyl, n-propyl, tetrahydro-2-furanylmethyl, trifluoromethylsulfonyl, N-carbethoxypiperidyl; or NR³R⁴ represent together 4-acetylpiperazinyl, 4-t-butoxycarbonylpiperazinyl, 2-(3,4-dihydro-2(1H)isoquinolinyl), (2R,6S)-2,6-dimethylmorpholinyl, (2R)-2,4-dimethyl-1-piperazinyl, 2-hydroxy-3-oxomorpholinyl, imidazolyl, 2-methyl-3-oxomorpholinyl, 4-methyl-2-oxopiperazinyl, 4-methylpiperazinyl, morpholinyl, (1S,4S)-2-oxa-5-aza-bicyclo[2.2.1]hept-5-yl, 2-oxoimidazolinyl, 3-oxomorpholinyl, 3-oxo-1,4-oxazepinyl, 2-oxooxazolinyl, piperazinyl; piperidinyl; pyrrolidinyl; pyrrolidonyl, thiomorpholinyl; 1,1-dioxido-thiomorpholinyl;

OCONR³R⁴, wherein R³ and R⁴ are each independently selected from ethyl, hydrogen or form together with the N-atom to which they are attached morpholinyl;

R⁵O, wherein R⁵ is acetyl, benzoyl, benzyl, ethyl, 2-fluoroethyl, 2-furylcarbonyl, hydrogen, isobutyryl, isopropyl, methyl, 2-carbomethoxyphenyl, methylsulfonyl, phenyl, n-propionyl, 3-pyridinyl, 2,2,2-trifluoroethyl;

with the proviso that when:

X is CH₂, Y is a single bond, then R² is not n-propyl;

X is CO, Y is a single bond, R² is ethoxy, B is methyl, then T is not 3-chloro-2-methylphenyl, 1,1'-biphenyl-4-yl, 4-n-propylphenyl, 2,4-dichloro-6-methylphenyl, and 2,4,6-trichlorophenyl.

When X is CH₂ and Y is CH₂, then it is preferred that:

R² is selected from n-propyl, azido, bromo, chloro, 2-pyridinylsulfanyl, 3-oxo-4-morpholinolinylmethylene, ethoxycarbonyl, 5-methyl-1,3,4-oxadiazol-2-yl, hydroxymethyl, 2-hydroxyethylaminomethyl, methylsulfonyloxymethyl;

NR³R⁴, wherein R³ and R⁴ are either each independently selected from acetyl, benzhydryl, 1,3-benzodioxol-5-ylmethyl, benzyl, 3-chloro-2-methylphenylsulfonyl, cyclohexyl, cyclohexylmethyl, cyclopropanecarbonyl, ethyl, 2-furylcarbonyl, 2-furylmethyl, hydrogen, 2-hydroxyethyl, 2-(1H-indol-3-yl)ethyl, isopropyl, methoxy, 2-methoxyethyl, methyl, 4-(1-methylimidazolyl)sulfonyl, methylsulfonyl, phenyl, (1S)-phenylethyl, n-propyl, tetrahydro-2-furanylmethyl, trifluoromethylsulfonyl, N-carbethoxypiperidyl; or NR³R⁴ represent together 4-acetylpiperazinyl, 4-t-butoxycarbonylpiperazinyl, 2-(3,4-dihydro-2(1H)isoquinolinyl), (2R,6S)-2,6-dimethylmorpholinyl, (2R)-2,4-dimethyl-1-piperazinyl, 2-hydroxy-3-oxomorpholinyl, imidazolyl, 2-methyl-3-oxomorpholinyl, 4-methyl-2-oxopiperazinyl, 4-methylpiperazinyl, morpholinyl, (1S,4S)-2-oxa-5-aza-bicyclo[2.2.1]hept-5-yl, 2-oxoimidazolinyl, 3-oxomorpholinyl, 3-oxo-1,4-oxazepinyl, 2-oxooxazolinyl, piperazinyl; piperidinyl; pyrrolidinyl; pyrrolidonyl, thiomorpholinyl; 1,1-dioxido-thiomorpholinyl;

OCONR³R⁴, wherein R³ and R⁴ are each independently selected from ethyl, hydrogen or form together morpholinyl;

R⁵O, wherein R⁵ is acetyl, benzoyl, benzyl, ethyl, 2-fluoroethyl, 2-furylcarbonyl, hydrogen, isobutyryl, isopropyl, methyl, 2-carbomethoxyphenyl, methylsulfonyl, phenyl, n-propionyl, 3-pyridinyl, 2,2,2-trifluoroethyl.

When X is CH₂ and Y is a single bond, then it is preferred that R² is selected from azido, bromo, chloro, 2-pyridinylsulfanyl, 3-oxo-4-morpholinolinylmethylene, ethoxycarbonyl, 5-methyl-1,3,4-oxadiazol-2-yl, hydroxymethyl, 2-hydroxyethylaminomethyl, methylsulfonyloxymethyl;

NR³R⁴, wherein R³ and R⁴ are each independently selected from acetyl, benzhydryl, 1,3-benzodioxol-5-ylmethyl, benzyl, 3-chloro-2-methylphenylsulfonyl, cyclohexyl, cyclohexylmethyl, cyclopropanecarbonyl, ethyl, 2-furylcarbonyl, 2-furylmethyl, hydrogen, 2-hydroxyethyl, 2-(1H-indol-3-yl)ethyl, isopropyl, methoxy, 2-methoxyethyl, methyl, 4-(1-methylimidazolyl)sulfonyl, methylsulfonyl, phenyl, (1S)-phenylethyl, n-propyl, tetrahydro-2-furanylmethyl, trifluoromethylsulfonyl, N-carbethoxypiperidyl; or NR³R⁴ represent together 4-acetylpiperazinyl, 4-t-butoxycarbonylpiperazinyl, 2-(3,4-dihydro-2(1H)isoquinolinyl), (2R,6S)-2,6-dimethylmorpholinyl, (2R)-2,4-dimethyl-1-piperazinyl, 2-hydroxy-3-oxomorpholinyl, imidazolyl, 2-methyl-3-oxomorpholinyl, 4-methyl-2-oxopiperazinyl, 4-methylpiperazinyl, morpholinyl, (1S,4S)-2-oxa-5-aza-bicyclo[2.2.1]hept-5-yl, 2-oxoimidazolinyl, 3-oxomorpholinyl, 3-oxo-1,4-oxazepinyl, 2-oxooxazolinyl, piperazinyl; piperidinyl; pyrrolidinyl; pyrrolidonyl, thiomorpholinyl; 1,1-dioxido-thiomorpholinyl;

OCONR³R⁴, wherein R³ and R⁴ are each independently selected from ethyl, hydrogen or form together with the N-atom to which they are attached morpholinyl;

R⁵O, wherein R⁵ is acetyl, benzoyl, benzyl, ethyl, 2-fluoroethyl, 2-furylcarbonyl, hydrogen, isobutyryl, isopropyl, methyl, 2-carbomethoxyphenyl, methylsulfonyl, phenyl, n-propionyl, 3-pyridinyl, 2,2,2-trifluoroethyl.

When X is CH₂, Y is a single bond, R² is methyl and B is methyl, then it is preferred that T is selected from 5-chloro-1,3-dimethyl-1H-pyrazol-4-yl; 4-chloro-2,3,1-benzoxadiazolyl; 5-(dimethylamino)-1-naphthyl; 1-methylimidazol-4-yl; 1-naphthyl; 2-naphthyl; 8-quinolinyl;

thienyl substituted with one or more of (benzoylamino)methyl, bromo, chloro, 3-isoxazolyl, 2-(methylsulfanyl)-4-pyrimidinyl, 1-methyl-5-(trifluoromethyl)pyrazol-3-yl, phenylsulfonyl, pyridyl;

phenyl substituted with either:

(i) one or more of 3-acetylaminophenyl, 3-acetylphenyl, benzeneamino, 1,3-benzodioxol-5-yl, 2-benzofuryl, benzylamino, 3,5-bis(trifluoromethyl)phenyl, bromo, butoxy, carboxy, 4-carboxyphenyl, 3-chloro-2-cyanophenoxy, 4-chlorophenyl, 5-chloro-2-thienyl, cyano, 3,4-dichlorophenyl, ({[4-(2-ethoxy-2-oxoethyl)-1,3-thiazol-2-yl]amino}carbonyl), fluoro, 5-fluoro-2-methoxyphenyl, 2-furyl, hydrogen, iodo, isopropyl, methanesulfonyl, methoxy, methyl, 4-methyl-1-piperazinyl, 4-methyl-1-piperidinyl, 4-methylsulfanylphenyl, 5-methyl-2-thienyl, 4-morpholinyl, nitro, 3-nitrophenyl, phenoxy, phenyl, n-propyl, 4-pyridyl, 3-pyridylmethylamino, 1-pyrrolidinyl, 2-thienyl, 3-thienyl, 2-thienylmethylamino, trifluoromethoxy, 4-trifluoromethoxyphenyl, trifluoromethyl; or (ii) one or more of 3-acetylaminophenyl, 3-acetylphenyl, benzeneamino, 1,3-benzodioxol-5-yl, 2-benzofuryl, benzylamino, 3,5-bis(trifluoromethyl)phenyl, bromo, butoxy, carboxy, chloro, 4-carboxyphenyl, 3-chloro-2-cyanophenoxy, 4-chlorophenyl, 5-chloro-2-thienyl, cyano, 3,4-dichlorophenyl, ({[4-(2-ethoxy-2-oxoethyl)-1,3-thiazol-2-yl]amino}carbonyl), fluoro, 5-fluoro-2-methoxyphenyl, 2-furyl, hydrogen, iodo, isopropyl, methanesulfonyl, methoxy, 4-methyl-1-piperazinyl, 4-methyl-1-piperidinyl, 4-methylsulfanylphenyl, 5-methyl-2-thienyl, 4-morpholinyl, nitro, 3-nitrophenyl, phenoxy, phenyl, n-propyl, 4-pyridyl, 3-pyridylmethylamino, 1-pyrrolidinyl, 2-thienyl, 3-thienyl, 2-thienylmethylamino, trifluoromethoxy, 4-trifluoromethoxyphenyl, trifluoromethyl; or (iii) one or more chloro and, in positions 3, 4, 5, one or more methyl.

When X is CO and Y is a single bond, then it is preferred that $R^2$ is selected from n-propyl, azido, bromo, chloro, 2-pyridinylsulfanyl, 3-oxo-4-morpholinolinylmethylene, ethoxycarbonyl, 5-methyl-1,3,4-oxadiazol-2-yl, hydroxymethyl, 2-hydroxyethylaminomethyl, methylsulfonyloxymethyl;

$NR^3R^4$, wherein $R^3$ and $R^4$ are each independently selected from acetyl, benzhydryl, 1,3-benzodioxol-5-ylmethyl, benzyl, 3-chloro-2-methylphenylsulfonyl, cyclohexyl, cyclohexylmethyl, cyclopropanecarbonyl, ethyl, 2-furylcarbonyl, 2-furylmethyl, hydrogen, 2-hydroxyethyl, 2-(1H-indol-3-yl)ethyl, isopropyl, methoxy, 2-methoxyethyl, methyl, 4-(1-methylimidazolyl)sulfonyl, methylsulfonyl, phenyl, (1S)-phenylethyl, n-propyl, tetrahydro-2-furanylmethyl, trifluoromethylsulfonyl, N-carbethoxypiperidyl; or $NR^3R^4$ represent together 4-acetylpiperazinyl, 4-t-butoxycarbonylpiperazinyl, 2-(3,4-dihydro-2(1H)isoquinolinyl), (2R,6S)-2,6-dimethylmorpholinyl, (2R)-2,4-dimethyl-1-piperazinyl, 2-hydroxy-3-oxomorpholinyl, imidazolyl, 2-methyl-3-oxomorpholinyl, 4-methyl-2-oxopiperazinyl, 4-methylpiperazinyl, morpholinyl, (1S,4S)-2-oxa-5-aza-bicyclo[2.2.1]hept-5-yl, 2-oxoimidazolinyl, 3-oxomorpholinyl, 3-oxo-1,4-oxazepinyl, 2-oxooxazolinyl, piperazinyl; piperidinyl; pyrrolidinyl; pyrrolidonyl, thiomorpholinyl; 1,1-dioxido-thiomorpholinyl;

$OCONR^3R^4$, wherein $R^3$ and $R^4$ are each independently selected from ethyl, hydrogen or form together with the N-atom to which they are attached morpholinyl;

$R^5O$, wherein $R^5$ is acetyl, benzoyl, benzyl, ethyl, 2-fluoroethyl, 2-furylcarbonyl, hydrogen, isobutyryl, isopropyl, methyl, 2-carbomethoxyphenyl, methylsulfonyl, phenyl, n-propionyl, 3-pyridinyl, 2,2,2-trifluoroethyl;

When X is CO and Y is a single bond and $R^2$ is ethoxy, then it is preferred that T is selected from 5-chloro-1,3-dimethyl-1H-pyrazol-4-yl; 4-chloro-2,3,1-benzoxadiazolyl; 5-(dimethylamino)-1-naphthyl; 1-methylimidazol-4-yl; 1-naphthyl; 2-naphthyl; 8-quinolinyl;

thienyl substituted with one or more of (benzoylamino) methyl, bromo, chloro, 3-isoxazolyl, 2-(methylsulfanyl)-4-pyrimidinyl, 1-methyl-5-(trifluoromethyl)pyrazol-3-yl, phenylsulfonyl, pyridyl;

phenyl substituted with either:
(i) one or more of acetylamino, 3-acetylaminophenyl, 3-acetylphenyl, benzeneamino, 1,3-benzodioxol-5-yl, 2-benzofuryl, benzylamino, 3,5-bis(trifluoromethyl)phenyl, bromo, butoxy, carboxy, 4-carboxyphenyl, 3-chloro-2-cyanophenoxy, 4-chlorophenyl, 5-chloro-2-thienyl, cyano, 3,4-dichlorophenyl, ({[4-(2-ethoxy-2-oxoethyl)-1,3-thiazol-2-yl]amino}carbonyl), fluoro, 5-fluoro-2-methoxyphenyl, 2-furyl, hydrogen, iodo, isopropyl, methanesulfonyl, methoxy, 4-methyl-1-piperazinyl, 4-methyl-1-piperidinyl, 4-methylsulfanylphenyl, 5-methyl-2-thienyl, 4-morpholinyl, nitro, 3-nitrophenyl, phenoxy, 4-pyridyl, 3-pyridylmethylamino, 1-pyrrolidinyl, 2-thienyl, 3-thienyl, 2-thienylmethylamino, trifluoromethoxy, 4-trifluoromethoxyphenyl, trifluoromethyl;
(ii) one or more of methyl;
(iii) one or more of chloro, phenyl and n-propyl in either position, and methyl in any of positions 3, 4 or 5;
(iv) one or more of n-propyl and phenyl in any of positions 2, 3, 5 or 6.

Specific examples of compounds according to the present invention are given above and also the following compound:
(2-{[(3-chloro-2-methylphenyl)sulfonyl]amino}-1,3-thiazol-5-yl)acetic acid (Example 3).

Another object of the present invention is a pharmaceutical composition comprising at least one compound of formula (I) as defined above, and a pharmaceutically acceptable carrier.

Also within the scope of this invention is a method for making a compound of formula (I). The method includes taking any intermediate compound delineated herein, reacting it with any one or more reagents to form a compound of formula (I) including any processes specifically delineated herein.

Other features and advantages of the invention will be apparent from the detailed description and the claims.

DETAILED DESCRIPTION OF THE INVENTION

The compounds according to the present invention may be used in several indications which involve 11-β-hydroxysteroid dehydrogenase type 1 enzyme. Thus, the compounds according to the present invention may be used against dementia (see WO97/07789), osteoporosis (see Canalis E 1996, Mechanisms of glucocorticoid action in bone: implications to glucocorticoid-induced osteoporosis, Journal of Clinical Endocrinology and Metabolism, 81, 3441–3447) and may also be used disorders in the immune system (see Franchimont et al, "Inhibition of Th1 immune response by glucocorticoids: dexamethasone selectively inhibits IL-12-induced Stat 4 phosphorylation in T lymphocytes", The journal of Immunology 2000, Feb. 15, vol 164 (4), pages 1768–74) and also in the above listed indications.

The various terms used, separately and in combinations, in the above definition of the compounds having the formula (I) will be explained.

The term "aryl" in the present description is intended to include aromatic rings (monocyclic or bicyclic) having from 6 to 10 ring carbon atoms, such as phenyl (Ph) and naphthyl, which optionally may be substituted by $C_{1-6}$-alkyl. Examples of substituted aryl groups are benzyl, and 2-methylphenyl.

The term "heteroaryl" means in the present description a monocyclic, bi- or tricyclic aromatic ring system (only one ring need to be aromatic) having from 5 to 14, preferably 5 to 10 ring atoms such as 5, 6, 7, 8, 9 or 10 ring atoms (mono- or bicyclic), in which one or more of the ring atoms are other than carbon, such as nitrogen, sulfur, oxygen and selenium as part of the ring system. Examples of such heteroaryl rings are pyrrole, imidazole, thiophene, furan, thiazole, isothiazole, thiadiazole, oxazole, isoxazole, oxadiazole, pyridine, pyrazine, pyrimidine, pyridazine, pyrazole, triazole, tetrazole, chroman, isochroman, quinoline, quinoxaline, isoquinoline, phthalazine, cinnoline, quinazoline, indole, isoindole, indoline, isoindoline, benzothiophene, benzofuran, isobenzofuran, benzoxazole, 2,1,3-benzoxadiazole, benzothiazole, 2,1,3-benzothiazole, 2,1,3-benzoselenadiazole, benzimidazole, indazole, benzodioxane, indane, 1,2,3,4-tetrahydroquinoline, 3,4-dihydro-2H-1,4-benzoxazine, 1,5-naphthyridine, 1,8-naphthyridine, acridine, fenazine and xanthene.

The term "heterocyclic" in the present description is intended to include unsaturated as well as partially and fully saturated mono-, bi- and tricyclic rings having from 4 to 14, preferably 4 to 10 ring atoms having one or more heteroatoms (e.g., oxygen, sulfur, or nitrogen) as part of the ring system and the remainder being carbon, such as, for example, the heteroaryl groups mentioned above as well as the corresponding partially saturated or fully saturated heterocyclic rings. Exemplary saturated heterocyclic rings are azetidine, pyrrolidine, piperidine, piperazine, morpholine, thiomorpholine and 1,4-oxazepane.

$C_{1-6}$-alkyl in the compound of formula (I) according to the present application, which may be straight, branched or cyclic, is preferably $C_{1-4}$-alkyl. Exemplary alkyl groups include methyl, ethyl, n-propyl, isopropyl, n-butyl, sec-butyl, tert-butyl, pentyl, isopentyl, hexyl, isohexyl, and cyclohexyl. For parts of the range "$C_{1-6}$-alkyl" all subgroups thereof are contemplated such as $C_{1-5}$-alkyl, $C_{1-4}$-alkyl, $C_{1-3}$-alkyl, $C_{1-2}$-alkyl, $C_{2-6}$-alkyl, $C_{2-5}$-alkyl, $C_{2-4}$-alkyl, $C_{2-3}$-alkyl, $C_{3-6}$-alkyl, $C_{4-5}$-alkyl, etc.

$C_{1-6}$-alkoxy, in the compound of formula (I) according to the present application may be straight or branched, is preferably $C_{1-4}$-alkoxy. Exemplary alkoxy groups include methoxy, ethoxy, propoxy, isopropoxy, butoxy, sec-butoxy, tert-butoxy, pentyloxy, isopentyloxy, hexyloxy, and isohexyloxy. For parts of the range "$C_{1-6}$-alkoxy" all subgroups thereof are contemplated such as $C_{1-5}$-alkoxy, $C_{1-4}$-alkoxy, $C_{1-3}$-alkoxy, $C_{1-2}$-alkoxy, $C_{2-6}$-alkoxy, $C_{2-5}$-alkoxy, $C_{2-4}$-alkoxy, $C_{2-3}$-alkoxy, $C_{3-6}$-alkoxy, $C_{4-5}$-alkoxy, etc.

$C_{1-6}$-acyl, in the compound of formula (I) according to the present application may be saturated or unsaturated and is preferably $C_{1-4}$-acyl. Exemplary acyl groups include formyl, acetyl, propionyl, butyryl, isobutyryl, valeryl, isovaleryl, butenoyl (e.g. 3-butenoyl), hexenoyl (e.g. 5-hexenoyl). For parts of the range "$C_{1-6}$-acyl" all subgroups thereof are contemplated such as $C_{1-5}$-acyl, $C_{1-4}$-acyl, $C_{1-3}$-acyl, $C_{1-2}$-acyl, $C_{2-6}$-acyl, $C_{2-5}$-acyl, $C_{2-4}$-acyl, $C_{2-3}$-acyl, $C_{3-6}$-acyl, $C_{4-5}$-acyl, etc.

$C_{2-6}$-alkenyl in the compound of formula (I) according to the present application, which may be straight, branched or cyclic, is preferably $C_{2-4}$-alkenyl. Exemplary alkenyl groups include vinyl, 1-propenyl, 2-propenyl, isopropenyl, 1-butenyl, 2-butenyl, 1-pentenyl, 2-pentenyl, 1-hexenyl, 2-hexenyl, and 1-cyclohexenyl. For parts of the range "$C_{2-6}$-alkenyl" all subgroups thereof are contemplated such as $C_{2-5}$-alkenyl, $C_{2-4}$-alkenyl, $C_{2-3}$-alkenyl, $C_{3-6}$-alkenyl, $C_{4-5}$-alkenyl, etc.

The term "halogen" in the present description is intended to include fluorine, chlorine, bromine and iodine.

The term "sulfanyl" in the present description means a thio group.

With the expression mono- or di-substituted is meant in the present description that the functionalities in question may be substituted with independently H, $C_{1-6}$-acyl, $C_{2-6}$-alkenyl, $C_{1-6}$-(cyclo)alkyl, aryl, pyridylmethyl, or heterocyclic rings e.g. azetidine, pyrrolidine, piperidine, piperazine, morpholine and thiomorpholine, which heterocyclic rings optionally may be substituted with $C_{1-6}$-alkyl.

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic administration to a subject for the treatment of disease, 11βHSD1 inhibition, 11βHSD1-mediated disease).

The term "prodrug forms" in the present description means a pharmacologically acceptable derivative, such as an ester or an amide, which derivative is biotransformed in the body to form the active drug (see Goodman and Gilman's, The Pharmacological basis of Therapeutics, $8^{th}$ ed., McGraw-Hill, Int. Ed. 1992, "Biotransformation of Drugs", p. 13–15).

"Pharmaceutically acceptable" means in the present description being useful in preparing a pharmaceutical composition that is generally safe, non-toxic and neither biologically nor otherwise undesirable and includes being useful for veterinary use as well as human pharmaceutical use.

"Pharmaceutically acceptable salts" mean in the present description salts which are pharmaceutically acceptable, as defined above, and which possess the desired pharmacological activity. Such salts include acid addition salts formed with organic and inorganic acids, such as hydrogen chloride, hydrogen bromide, hydrogen iodide, sulfuric acid, phosphoric acid, acetic acid, glycolic acid, maleic acid, malonic acid, oxalic acid, methanesulfonic acid, trifluoroacetic acid, fumaric acid, succinic acid, tartaric acid, citric acid, benzoic acid, ascorbic acid and the like. Base addition salts may be formed with organic and inorganic bases, such as sodium, ammonia, potassium, calcium, ethanolamine, diethanolamine, N-methylglucamine, choline and the like. Included in the invention are pharmaceutically acceptable salts or compounds of any of the formulae herein.

Pharmaceutical compositions according to the present invention contain a pharmaceutically acceptable carrier together with at least one of the compounds comprising the formula (I) as described herein above, dissolved or dispersed therein as an active, antimicrobial, ingredient. In a preferred embodiment, the therapeutic composition is not immunogenic when administered to a human patient for therapeutic purposes, unless that purpose is to induce an immune response.

The preparation of a pharmacological composition that contains active ingredients dissolved or dispersed therein is well understood in the art. Typically such compositions are prepared as sterile injectables either as liquid solutions or suspensions, aqueous or non-aqueous, however, solid forms suitable for solution, or suspensions, in liquid prior to use can also be prepared. The preparation can also be emulsified.

The active ingredient may be mixed with excipients, which are pharmaceutically acceptable and compatible with the active ingredient and in amounts suitable for use in the therapeutic methods described herein. Suitable excipients are, for example, water, saline, dextrose, glycerol, ethanol or the like and combinations thereof. In addition, if desired, the composition may contain minor amounts of auxiliary substances such as wetting or emulsifying agents, pH buffering agents and the like which enhance the effectiveness of the active ingredient. Adjuvants may also be present in the composition.

Pharmaceutically acceptable carriers are well known in the art. Exemplary of liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, propylene glycol, polyethylene glycol and other solutes.

Liquid compositions can also contain liquid phases in addition to and to the exclusion of water. Exemplary of such additional liquid phases are glycerine, vegetable oils such as cottonseed oil, organic esters such as ethyl oleate, and water-oil emulsions.

The pharmaceutical composition according to one of the preferred embodiments of the present invention comprising compounds comprising the formula (I), may include pharmaceutically acceptable salts of that component therein as set out above. Pharmaceutically acceptable salts include the acid addition salts (formed with the free amino groups of the polypeptide) that are formed with inorganic acids such as, for example, hydrochloric or phosphoric acids, or such organic acids as acetic acid, tartaric acid, mandelic acid and the like. Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine and the like.

The preparations according to the preferred embodiments may be administered orally, topically, intraperitoneally, intraarticularly, intracranially, intradermally, intramuscularly, intraocularly, intrathecally, intravenously, subcutaneously. Other routes are known to those of ordinary skill in the art.

The orally administrable compositions according to the present invention may be in the form of tablets, capsules, powders, granules, lozenges, liquid or gel preparations, such as oral, topical or sterile parenteral solutions or suspensions. Tablets and capsules for oral administration may be in unit dose presentation form and may contain conventional excipients such as binding agents, for example syrup, acacia, gelatin, sorbitol, traganath or polyvinyl-pyrrolidone; fillers e.g. lactose, sugar, maize-starch, calcium phosphate, sorbitol or glycine; tabletting lubricant e.g. magnesium stearate, talc, polyethylene glycol or silica; disintegrants e.g. potato starch, or acceptable wetting agents such as sodium lauryl sulfate. The tablets may be coated according to methods well known in normal pharmaceutical practice. Oral liquid preparations may be in the form of e.g. aqueous or oily suspensions, solutions, emulsions, syrups or elixirs or may be presented as a dry product for reconstitution with water or other suitable vehicle before use. Such liquid preparations may contain conventional additives such as suspending agents, e.g. sorbitol, syrup, methyl cellulose, glucose syrup, gelatin hydrogenated edible fats; emulsifying agents e.g. lecithin, sorbitan monooleate or acacia, non-aqueous vehicles (which may include edible oils), e.g. almond oil, fractionated coconut oil, oily esters such as glycerine, propylene glycol, or ethyl alcohol; preservatives e.g. methyl or propyl p-hydroxybenzoate or sorbic acid, and if desired conventional flavouring or colouring agents.

"An effective amount" refers to an amount of a compound which confers a therapeutic effect on the treated subject. The therapeutic effect may be objective (i.e., measurable by some test or marker) or subjective (i.e., subject gives an indication of or feels an effect). A pharmaceutical composition according to the present invention, may comprise typically an amount of at least 0.1 weight percent of compound comprising the formula (I) per weight of total therapeutic composition. A weight percent is a ratio by weight of total composition. Thus, for example, 0.1 weight percent is 0.1 grams of compound comprising the formula (I) per 100 grams of total composition. A suitable daily oral dose for a mammal, preferably a human being, may vary widely depending on the condition of the patient. However a dose of compound comprising the formula (I) of about 0.1 to 300 mg/kg body weight may be appropriate.

The compositions according to the present invention may also be used veterinarily and thus they may comprise a veterinarily acceptable excipient or carrier. The compounds and compositions may be thus administered to animals, e.g., cats, dogs, or horses, in treatment methods.

The compounds of the present invention in labelled form, e.g. isotopically labelled, may be used as a diagnostic agent.

This invention relates to methods of making compounds of any of the formulae herein comprising reacting any one or more of the compounds of the formulae delineated herein, including any processes delineated herein. The compounds of formula (I) above may be prepared by, or in analogy with, conventional methods, and especially according to or in analogy with the following methods. Further, the pharmacology in-vitro was studied using the following reagents and methods.

The chemicals used in the synthetic routes delineated herein may include, for example, solvents, reagents, catalysts, and protecting group and deprotecting group reagents. The methods described above may also additionally include steps, either before or after the steps described specifically herein, to add or remove suitable protecting groups in order to ultimately allow synthesis of the compounds. In addition, various synthetic steps may be performed in an alternate sequence or order to give the desired compounds. Synthetic chemistry transformations and protecting group methodologies (protection and deprotection) useful in synthesizing applicable compounds are known in the art and include, for example, those described in R. Larock, *Comprehensive Organic Transformations*, VCH Publishers (1989); T. W. Greene and P. G. M. Wuts, *Protective Groups in Organic Synthesis*, 3$^{rd}$ Ed., John Wiley and Sons (1999); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof.

All publications mentioned herein are hereby incorporated by reference. By the expression "comprising" means "including but not limited to." Thus, other non-mentioned substances, additives or carriers may be present.

The invention will now be described in reference to the following Examples. These Examples are not to be regarded as limiting the scope of the present invention, but shall only serve in an illustrative manner.

EXAMPLES

Experimental Methods
Scintillation Proximity Assay

[1,2(n)-$^3$H]-cortisone was purchased from Amersham Pharmacia Biotech. Anti-cortisol monoclonal mouse antibody, clone 6D6.7 was obtained from Immunotech and Scintillation proximity assay (SPA) beads coated with monoclonal antimouse antibodies were from Amersham Pharmacia Biotech. NADPH, tetrasodium salt was from Calbiochem and glucose-6-phosphate (G-6-P) was supplied by Sigma. The human 11-β-hydroxysteroid dehydrogenase type-1 enzyme (11-β-HSD$_1$) was expressed in *Pichia pastoris*. 18-β-glycyrrhetinic acid (GA) was obtained from Sigma. The serial dilutions of the compounds were performed on a Tecan Genesis RSP 150. Compounds to be tested were dissolved in DMSO (1 mM) and diluted in 50 mM Tris-HCl, pH 7.2 containing 1 mM EDTA.

The multiplication of plates was done on a WallacQuadra. The amount of the product [$^3$H]-cortisol, bound to the beads was determined in a Packard, Top Count microplate liquid scintillation counter.

The 11-β-HSD$_1$ enzyme assay was carried out in 96 well microtiter plates (Packard, Optiplate) in a total well volume of 220 μL and contained 30 mM Tris-HCl, pH 7.2 with 1 mM EDTA, a substrate mixture tritiated Cortisone/NADPH (175 nM/181 μM), G-6-P (1 mM) and inhibitors in serial dilutions (9 to 0.15 μM). Reactions were initiated by the addition of human 11-β-HSD$_1$, either as *Pichia pastoris* cell homogenate or microsomes prepared from *Pichia pastoris* (the final amount of enzyme used was varied between 0.057 to 0.11 mg/mL). Following mixing, the plates were shaken for 30 to 45 minutes at room temperature. The reactions were terminated with 10 µL 1 mM GA stop solution. Monoclonal mouse antibody was then added (10 µL of 4 µM) followed by 100 µL of SPA beads (suspended according to the manufacturers instructions). Appropriate controls were set up by omitting the 11-β-$HSD_1$ to obtain the non-specific binding (NSB) value.

The plates were covered with plastic film and incubated on a shaker for 30 minutes, at room temperature, before counting. The amount of [$^3$H]-cortisol, bound to the beads was determined in a microplate liquid scintillation counter.

The calculation of the $K_i$ values for the inhibitors was performed by use of Activity Base. The $K_i$ value is calculated from $IC_{50}$ and the $K_m$ value is calculated using the Cheng Prushoff equation (with reversible inhibition that follows the Michaelis-Menten equation): $K_i=IC_{50}(1+[S]/K_m)$ [Cheng, Y. C.; Prushoff, W. H. Biochem. Pharmacol. 1973, 22, 3099–3108]. The $IC_{50}$ is measured experimentally in an assay wherein the decrease of the turnover of cortisone to cortisol is dependent on the inhibition potential of each substance. The Ki values of the compounds of the present invention for the 11-β-HSD1 enzyme lie typically between about 10 nM and about 10 µM.

Compound Preparation

General:

For preparative straight phase HPLC purification a Phenomenex column (250×21.1 mm, 10 µm) was used on a Gilson system eluting with ethanol in chloroform (gradient from 0–10% in 10 min) with a flow of 20 mL/min. Column chromatography was performed on silica using Silica gel 60 (230–400 mesh), Merck. Melting points were determined on a Gallenkamp apparatus. Elemental analyses were recorded using a Vario EL instrument. HPLC analyses were performed using a Hypersil Elite column (150×4.6 mm, 3µ) with a flow of 3 mL/min on a Waters 600E system with monitoring at 254 nm. Reverse phase preparative HPLC was carried out on a 100×21.2 mm, 5µ Hypersil Elite column eluting with a gradient of 5% ACN in 95% water to 95% ACN in 5% water (0.2% TFA buffer) over 10 mins at a flow rate of 20 mL/min with the UV detector set at 254 nm. Thin layer chromatography was carried out using pre-coated silica gel F-254 plates (thickness 0.25 mm). Electrospray MS spectra were obtained on a Micromass platform LCMS spectrometer. Crude, worked up compounds were purified by flash column chromatography using pre packed silica SPE columns (10 g silica) on an Isco Foxy 200 Combiflash system, and a gradient of 16.67% ethyl acetate in hexane increasing incrementally to 100% ethyl acetate.

List of Abbreviations

ACN=acetonitrile
DCM=dichloromethane
DIEA=N,N-diisopropylethylamine
DMAP=4-dimethylaminopyridine
DME=ethyleneglycol dimethyl ether
DMF=dimethylformamide
DMSO=dimethyl sulfoxide
EDCI=1-(3-dimethylaminopropyl)-3-ethylcarbodiimide hydrochloride
EDTA=ethylenediaminetetraacetic acid
HCOOH=formic acid
HOAT=1-hydroxy-7-azabenzotriazole
HOBT=1-hydroxybenzotriazole hydrate
HPLC=high performance liquid chromatography
MTBE=tert-butyl methyl ether
RP LC-MS=reversed-phase liquid chromatography-mass spectrometry
TEA=triethylamine
TFA=trifluoroacetic acid
THF=tetrahydrofuran Sulfonamide Couplings:

Method A:

1 Eq of the 2-aminothiazole was dissolved in pyridine (0.5 M solution). The sulfonyl chloride (1.2 eq) was added and the reaction mixture was stirred at ambient temperature under nitrogen atmosphere for 15 h. The reaction mixture was poured into aqueous HCl (1 M). If the product precipitated it was collected on a filter and washed with aqueous HCl (1 M) and recrystallised from ethanol. In case an oil was obtained, the crude was extracted with DCM and worked up and purified using standard procedures.

Method B:

A solution of the 2-aminothiazole derivative (1 eq), triethylamine (2 eq) and DMAP (1 eq) in DMF (1 M) and DCM (0.225 M) was dispensed into a reaction vial. The sulfonyl chloride (1.2 eq) was dissolved in DCM (0.33 M) and added. The reaction mixtures were kept at room temperature over night. The mixture was then added to petroleum ether (10 times reaction volume). After some hours in refrigerator the supernatants were decanted and (a portion of) the residual materials were dissolved in DMSO-methanol-acetic acid (300 µL+500 µL+50 µL) and purified by preparative LCMS (acetonitrile-water gradients). The purest fractions were collected and lyophilized. Alternatively, the crude was isolated using extractive work-up and purified using standard procedures.

Saponifications:

Method C:

1 Eq of the ester was suspended in 95% ethanol (0.1 M) and treated with KOH (aqueous, 6 eq). Water was added until a clear solution was achieved. The reaction mixture was stirred for 2–3 h at ambient temperature. The solvent was removed under reduced pressure and the crude was redissolved in water. Addition of conc. HCl until pH 2 gave a precipitate which was collected on a filter and washed with cold water and dried.

Amide Couplings:

Method D:

The carboxylic acid ester was dissolved (0.05 M) in a large excess of the amine in 40 or 70% water-solution. The reaction mixture was stirred at ambient temperature over night. The solvent was removed under reduced pressure and the crude product was purified by flash column chromatography on silica gel eluting with methanol (0→6%) in DCM.

Method E:

The carboxylic acid was suspended in DCM (0.05M) followed by the addition of EDCI (1.1 eq), triethylamine (3 eq), DMAP (0.5 eq) and the amine of choice (1.2 eq). DMF was added when the starting materials did not dissolve properly. The reaction mixture was stirred at ambient temperature over night. The organic phase was washed with aqueous HCl (1 M), dried over sodium sulfate, filtered and evaporated in vacuo. The crude product amide was purified by flash column chromatography on silica gel, eluting with methanol (1→3→6%) in DCM or ethyl acetate.

Method F:

The carboxylic acid was suspended in DCM (0.1 M) and cooled to 0° C. under nitrogen (g) atmosphere. EDCI (1 eq), HOAT (1 eq) or HOBT (1 eq) was added, followed by TEA (2.2 eq). After 10 min, the amine of choice (1.2 eq) was added and the reaction mixture was allowed to warm to ambient temperature. After 5 h, the DCM phase was washed with aqueous HCl (1 M) and worked up and purified as described in METHOD E.

Method G:

Under $N_2$-atmosphere, aluminium chloride (1 eq) was suspended in DCM (0.1 M) and treated with the amine of choice (4 eq) at ambient temperature. After 10 min, the alkyl ester (1 eq) was added and the reaction mixture was stirred until starting material had been consumed (TLC). Quenching with saturated aqueous sodium hydrogen carbonate or aqueous HCl (1 M) and extractive workup with ethyl acetate gave the crude products which were then purified by flash chromatography on silica gel eluting with DCM/methanol mixtures.

Formation of Thiazole Ring:

Method H:

To a solution or suspension of an optionally substituted thiourea in ethanol (0.5 M), 1 equivalent of α-haloketone was added at room temperature. The reaction mixture was stirred in a sealed tube at 95° C. for 4 h, cooled, concentrated, redissolved in ethyl acetate, washed with saturated aqueous sodium hydrogen carbonate, dried over sodium sulfate and chromatographed on silica gel using petroleum-ether and ethyl acetate as eluents.

Method I:

To a 0.5 M solution of ketone (1 eq) and thiourea (2 eq) in ethanol at 60° C., 1 eq of iodine was added in one portion. The reaction tube was sealed and the reaction mixture was stirred at 100° C. for 16 hours. After evaporation of the solvent the residue was taken up in DCM, washed with saturated aqueous sodium hydrogen carbonate, dried with magnesium sulfate. Products were purified by chromatography on silica gel using a gradient of petroleum-ether/ethyl acetate from 8:1 to 2:1 for elution.

Acylations:

Method J:

To a solution of the alcohol in dry pyridine (0.3 M), 1.1 eq of acid chloride was added at 0° C. The reaction mixture was stirred at room temperature for 6 h, concentrated, co-evaporated with acetonitrile, re-dissolved in DCM, washed with aqueous HCl (0.5 M), dried with sodium sulfate and chromatographed on silica gel using petroleum-ether and ethyl acetate as eluents.

Carbamates:

Method K:

To a solution of the alcohol in dry pyridine (0.3 M), 1.5 eq of 4-nitrophenyl chloroformate (0.5 M in dry pyridine) was added at 0° C. After the reaction mixture was stirred at room temperature for 12 h, 5 eq of primary or secondary amine were added at 0° C. The solution was stirred at room temperature for 3 h, concentrated, co-evaporated with acetonitrile, re-dissolved in DCM, washed with aqueous HCl (0.5 M) and saturated aqueous sodium bicarbonate, dried with sodium sulfate and chromatographed on silica gel using DCM and methanol as eluents.

Sulfonyl Chlorides

Arylsulfonyl chlorides that were not commercially available were prepared from the aniline derivatives according to literature procedures (see for instance: Hoffman, R. V. (1981) Org. Synth. 60: 121).

2-amino-5-thiazoleacetic acid, ethyl ester is available from Ambinter, 46 quai Louis Bleriot, Paris, F-75016, France. The preparation thereof has been described in:

Aryl diazo compounds and diazonium salts as potential irreversible probes of the GABA receptor. Bouchet, Marie Jeanne; Rendon, Alvaro; Wermuth, Camille G.; Goeldner, Maurice; Hirth, Christian. Fac. Pharm., Univ. Louis Pasteur, Strasbourg, Fr. J. Med. Chem. (1987), 30(12), 2222–7. CODEN: JMCMAR ISSN: 0022–2623. Journal written in English. CAN 107:198180 AN 1987:598180 CAPLUS; and Growth regulating activity of some thiazole-, thiazoline-, and thiazolidineacetic acids. Garraway, J. L. Dep. Phys. Sci., Wye Coll., Ashford/Kent, Engl. Pestic. Sci. (1974), 5(2), 185–8. CODEN: PSSCBG Journal written in English. CAN 81:73315 AN 1974:473315 CAPLUS Preparation of Compounds in Examples 1–5

Example 1

3-chloro-2-methyl-N-[5-(2-morpholin-4-ylethyl)-1,3-thiazol-2-yl]benzenesulfonamide Step a—Preparation of 2-(2-amino-1,3-thiazol-5-yl)ethanol 2,3-dichlorotetrahydrofurane (5 g; 0,035 mol) and thiourea (2,7 g; 0,035 mol) were refluxed for 12 h in water (20 ml). Then 40 ml of 40% NaOH (aq) were added, the reaction mixture was cooled to room temperature and stirred for one hour. The formed precipitate was filtered off, dried at reduced pressure and recrystallized from EtOH/Et$_2$O. HCl, 2M in Et$_2$O, was added to form the HCl-salt which was isolated by filtration and dried. Yielded 3,8 g, 61%.

$^1$H NMR (400 MHz, DMSO-d$_6$) δ ppm 2.71 (t, J=4.88 Hz, 2 H) 3.53 (t, J=5.62 Hz, 2 H) 4.17 (s, 1 H) 7.06 (s, 1 H) 9.37 (s, 2 H). MS m/z: M+H 145

Step b—Preparation of 3-chloro-2-methyl-N-[5-(2-morpholin-4-ylethyl)-1,3-thiazol-2-yl]benzenesulfonamide 2-(2-amino-1,3-thiazol-5-yl)ethanol (0,16 g; 0,89 mmol), 3-chloro-2-methylbenzenesulfonyl chloride (0,62 g; 2,8 mmol) and NaOH (0,093 g; 2,3 mmol) were dissolved in 9 ml THF:H$_2$O (1:2) and stirred over night. The reaction mixture was extracted twice with dichloromethane and the organic layers was combined, dried over MgSO$_4$ and concentrated. The crude material was then stirred in morpholine (10 ml) over night. The reaction mixture was concentrated and purified on preparative RP LC-MS, then further purified on a preparative TLC-column (Trikonex, FlashTube™ 2008) eluted with CHCl$_3$/MeOH 40/3+triethylamine 1%. The substance was visualized by UV-light, the relevant band cut out and the silica-gel extracted with the eluent. Fitration and concentration yielded a product which was still found to contain a number of impurities. This was further purified on preparative RP LC-MS. Yield 0,8 mg.

$^1$H NMR (400 MHz, methanol-d$_4$) δ ppm 2.65 (m, 3 H) 3.10 (m, 4 H) 3.28 (m, 2 H) 3.45 (m, 2 H) 3.70 (m, 2 H) 4.02 (m, 2 H) 7.00 (m, 1 H) 7.24 (t, J=7.81 Hz, 1 H) 7.54 (d, J=8.06 Hz, 1 H) 7.91 (d, J=7.57 Hz, 1 H). MS m/z: M+H 402. HRMS (EI) calcd for C$_{16}$H$_{20}$ClN$_3$O$_3$S$_2$: 401.0635, found 401.0627.

Example 2

Methyl (2-{[(3-chloro-2-methylphenyl)sulfonyl]amino}-1,3-thiazol-5-yl)acetate

Step a—Preparation of Methyl 3-bromo-4-oxobutanoate

Firstly, methyl 4-oxobutanoate was synthesized from the commercially available methyl 4,4-dimethoxybutyrate according to a literature procedure; Will, S. G.; Magriotis, P.; Marinelli, E. R.; Dolan, J.; Johnson, F. *J. Org. Chem.*, 1985, 50, 5433–5434.

Secondly, methyl 3-bromo-4-oxobutanoate was obtained from methyl 4-oxobutanoate following a literature procedure; Aeberli, M.; Erlenmeyer. H. *Hel. Chim. Acta.*, 1950, 70, 503–505.

Step b—Preparation of Methyl (2{[(3-chloro-2-methylphenyl)sulfonyl]amino}-1,3-thiazol-5-yl)acetate N-(aminocarbonothioyl)-3-chloro-2-methylbenzenesulfonamide (0.4 g, 1.5 mmol) and methyl 3-bromo-4- oxobutanoate (0.3 g, 1.5 mmol), dissolved in pyridine (5 mL), were irradiated in a microwave oven for 2.5 min at 130° C. The solvent was removed under reduced pressure and the product separated from the starting materials using preparative HPLC (yield 0.2 g, 30%).

$^1$H NMR (400 MHz, CD$_3$OD) δ ppm 2.70 (s, 3 H) 3.69 (d, J=1.22 Hz, 2 H) 3.70 (s, 3 H) 6.98 (t, J=1.10 Hz, 1 H) 7.29 (t, J=8.30 Hz, 1 H) 7.57 (dd, J=8.06, 1.46 Hz, 1 H) 7.96 (m, 1 H). MS m/z: M+H 361.

Example 3

(2-{[(3-chloro-2-methylphenyl)sulfonyl]amino}-1,3-thiazol-5-yl)acetic acid

To methyl (2-{[(3-chloro-2-methylphenyl)sulfonyl]amino}-1,3-thiazol-5-yl)acetate (Example 2) (0.2 g, 0.55 mmol) dissolved in EtOH (5.5 mL) was added aqueous KOH (0.6 mL, 5.5 M). The reaction mixture was stirred at room temperature for 1 h. The solvent was then removed under reduced pressure and the crude product dissolved in water. The aqueous phase was acidified using conc. HCl so that the product precipitated. Filtration and washing with water (5 mL) afforded 0.2 g, 97% product. The product was used without any further purification.

Example 4

3-chloro-2-methyl-N-[5-(2-morpholin-4-yl-2-oxoethyl)-1,3-thiazol-2yl]benzenesulfonamide To a solution of (2-{[(3-chloro-2-methylphenyl)sulfonyl]amino}-1,3-thiazol-5-yl)acetic acid (Example 3) (0.09 g, 0.25 mmol) in CH$_2$Cl$_2$ (5.0 mL) and DMF (0.5 mL) were added EDCI (0.05 g, 0.27 mmol), DMAP (0.02 g, 0.12 mmol), triethylamine (0.1 mL, 0.75 mmol) and morpholine (0.03 mL, 0.30 mmol). The reaction mixture was stirred at room temperature overnight. The reaction mixture was then washed with 1 M HCl (2×15 mL) and the organic layer was collected. The organic phase was dried (MgSO$_4$) and concentrated under reduced pressure. Purification using preparative HPLC afforded the desired product (0.01 g) in 10% yield.

$^1$H NMR (400 MHz, acetone-d$_6$) δ ppm 2.67 (s, 3 H) 3.47–3.63 (m, 8 H) 3.82 (d, J=1.22 Hz, 2 H) 7.05 (t, J=1.22 Hz, 1 H) 7.33 (t, J=8.30 Hz, 1 H) 7.57 (m, 1 H) 7.98 (dd, J=8.06, 1.22 Hz, 1 H). MS m/z: M+H 416.

Example 5

2-(2-{[(3-chloro-2-methylphenyl)sulfonyl]amino}-1,3-thiazol-5-yl)-N,N-diisopropylacetamide To a solution of (2-{[(3-chloro-2-methylphenyl)sulfonyl]amino}-1,3-thiazol-5-yl)acetic acid (Example 3) (0.09 g, 0.25 mmol) in CH$_2$Cl$_2$ (5.0 mL) and DMF (0.5 mL) were added EDCI (0.05 g, 0.27 mmol), DMAP (0.02 g, 0.12 mmol), triethylamine (0.1 mL, 0.75 mmol) and diisopropylamine (0.04 mL, 0.30 mmol). The reaction mixture was stirred at room temperature overnight. The reaction mixture was then washed with 1 M HCl (2×15 mL) and the organic layer was collected. The organic phase was dried (MgSO$_4$) and concentrated under reduced pressure. Purification using preperative HPLC afforded the desired product (0.01 g) in 9% yield.

$^1$H NMR (400 MHz, CDCl$_3$) δ ppm 1.21 (d, J=6.10 Hz, 6 H) 1.34 (d, J=6.59 Hz, 6 H) 2.64 (s, 3 H) 3.61 (m, J=19.53 Hz, 1 H) 3.63 (s, 2 H) 3.89 (m, 1 H) 6.94 (s, 1 H) 7.23 (m, 1 H) 7.52 (d, J=7.81 Hz, 1 H) 8.04 (d, J=7.81 Hz, 1 H). MS m/z: M+H 430.

Various embodiments of the present invention have been described above but a person skilled in the art realizes further minor alterations which would fall into the scope of the present invention. The breadth and scope of the present invention should not be limited by any of the above-described exemplary embodiments, but should be defined only in accordance with the following claims and their equivalents.

What is claimed is:

1. A compound of Formula (I)

wherein
T is an aryl ring, optionally independently substituted by [R]n, wherein n is an integer 0–5, and R is hydrogen, aryl, optionally halogenated C$_{1-6}$-alkyl, optionally halogenated C$_{1-6}$-alkoxy, C$_{1-6}$-alkylsulfonyl, carboxy, cyano, nitro, halogen, aryloxy, arylsulfonyl, arylamino, wherein aryl and aryloxy residues are further optionally substituted in one or more positions independently of each other by C$_{1-6}$-acyl, C$_{1-6}$-alkylthio, cyano, nitro, hydrogen, halogen, optionally halogenated C$_{1-6}$-alkyl, optionally halogenated C$_{1-6}$-alkoxy, amide which is optionally mono- or di-substituted, (benzoylamino)methyl, carboxy, or 2-thienylmethylamino;
or T is selected from 5-(dimethylamino)-1-naphthyl and phenyl substituted with one or more of benzeneamino, benzylamino and 2-thienylmethylamino;
R$^1$ is hydrogen or C$_{1-6}$-alkyl;
X is CH$_2$ or CO;
Y is CO;
B is hydrogen, C$_{1-6}$-alkyl or dimethylaminomethyl;
R$^2$ is NR$^3$R$^4$, wherein R$^3$ and R$^4$ are each independently selected from hydrogen, ethyl, isopropyl, n-propyl, optionally halogenated C$_{1-6}$-alkylsulfonyl, C$_{1-6}$-alkoxy, 2-methoxyethyl, 2-hydroxyethyl, C$_{1-6}$-acyl, cyclohexylmethyl, cyclopropanecarbonyl, aryl, optionally halogenated arylsulfonyl or C$_{1-6}$-alkyl substituted with one or more aryl
or a salt, hydrate or solvate thereof.

2. The compound according to claim 1, wherein
T is selected from the group consisting of 5-(dimethylamino)-1-naphthyl; 1-naphthyl; 2-naphthyl; and
phenyl substituted with one or more of 3-acetylaminophenyl, 3-acetylphenyl, benzeneamino, benzylamino, 3,5-bis(trifluoromethyl)phenyl, bromo, butoxy, carboxy, chloro 4-carboxyphenyl, 3-chloro-2-cyanophenoxy, 4-chlorophenyl, cyano, 3,4-dichlorophenyl, fluoro, 5-fluoro-2-methoxyphenyl, hydrogen, iodo, isopropyl, methanesulfonyl, methoxy, methyl, 4-methylsulfanylphenyl, nitro, 3-nitrophenyl, phenoxy, phenyl, n-propyl, 2-thienylmethylamino, trifluoromethoxy, 4-trifluoromethoxyphenyl, trifluoromethyl;
R$^1$ is hydrogen or methyl;
X is CH$_2$ or CO;
Y is CO;
B is hydrogen, methyl or dimethylaminomethyl;

$R^2$ is $NR^3R^4$, wherein $R^3$ and $R^4$ are each independently selected from the group consisting of acetyl, benzhydryl, benzyl, 3-chloro-2-methylphenylsulfonyl, cyclohexyl, cyclohexylmethyl, cyclopropanecarbonyl, ethyl, hydrogen, 2-hydroxyethyl, isopropyl, methoxy, 2-methoxyethyl, methylsulfonyl, phenyl, (1S)-phenylethyl, n-propyl, and trifluoromethylsulfonyl.

3. A compound selected from the group consisting of:

2-(2-{[(3-chloro-2-methylphenyl)sulfonyl]amino}-1,3-thiazol-5-yl)-N-ethylacetamide 2-(2-{[(3-chloro-2-methylphenyl)sulfonyl]amino}-1,3-thiazol-5-yl)-N,N-diethylacetamide 2-(2-{[(3-chloro-2-methylphenyl)sulfonyl]amino}-1,3-thiazol-5-yl)acetamide N-[2-(2-{[(3-chloro-2-methylphenyl)sulfonyl]amino}-1,3-thiazol-5-yl)ethyl]-N-ethylacetamide 2-{2-[(1,1'-biphenyl-4-ylsulfonyl)amino]-1,3-thiazol-5-yl}-N,N-diethylacetamide N,N-diethyl-2-(2-{[(4-propylphenyl)sulfonyl]amino}-1,3-thiazol-5-yl)acetamide 2-(2-{[(2,4-dichloro-6-methylphenyl)sulfonyl]amino}-1,3-thiazol-5-yl)-N,N-diethylacetamide 2-{2-[(1,1'-biphenyl-4-ylsulfonyl)amino]-1,3-thiazol-5-yl}-N,N-diisopropylacetamide N,N-diisopropyl-2-(2-{[(4-propylphenyl)sulfonyl]amino)-1,3-thiazol-5-yl)acetamide 2-(2-{[(2,4-dichloro-6-methylphenyl)sulfonyl]amino}-1,3-thiazol-5-yl)-N,N-diisopropylacetamide 2-(2-{[(3-chloro-2-methylphenyl)sulfonyl]amino}-1,3-thiazol-5-yl)-N,N-dipropylacetamide 2-(2-{[(3-chloro-2-methylphenyl)sulfonyl]amino}-1,3-thiazol-5-yl)-N,N diisopropylacetamide and N-[2-(2-{[(3-chloro-2-methylphenyl)sulfonyl]amino}-1,3-thiazol-5-yl )ethyl]acetamide.

4. A pharmaceutical composition comprising a compound of formula (I) as defined in claim 1, and a pharmaceutically acceptable carrier.

* * * * *